(12) United States Patent
Zhao et al.

(10) Patent No.: US 7,723,351 B2
(45) Date of Patent: *May 25, 2010

(54) MULTI-ARM POLYMERIC CONJUGATES OF 7-ETHYL-10-HYDROXYCAMPTOTHECIN FOR TREATMENT OF BREAST, COLORECTAL, PANCREATIC, OVARIAN AND LUNG CANCERS

(75) Inventors: Hong Zhao, Edison, NJ (US); Maria Belen Rubio, Somerset, NJ (US); Dechun Wu, Bridgewater, NJ (US); Puja Sapra, Edison, NJ (US)

(73) Assignee: Enzon Pharmaceuticals, Inc., Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/274,474

(22) Filed: Nov. 20, 2008

(65) Prior Publication Data

US 2009/0074706 A1    Mar. 19, 2009

Related U.S. Application Data

(63) Continuation of application No. 11/704,607, filed on Feb. 9, 2007, now Pat. No. 7,462,627.

(60) Provisional application No. 60/772,464, filed on Feb. 9, 2006, provisional application No. 60/804,391, filed on Jun. 9, 2006, provisional application No. 60/844,938, filed on Sep. 15, 2006, provisional application No. 60/864,516, filed on Nov. 6, 2006.

(51) Int. Cl.
*A61K 31/4745* (2006.01)
*C07D 491/22* (2006.01)

(52) U.S. Cl. .................. 514/283; 546/48; 514/280

(58) Field of Classification Search .............. 514/283, 514/280; 546/48
See application file for complete search history.

(56) References Cited

U.S. PATENT DOCUMENTS

| 4,473,692 | A | 9/1984 | Miyasaka et al. |
| 5,614,549 | A | 3/1997 | Greenwald et al. |

(Continued)

FOREIGN PATENT DOCUMENTS

| EP | 0757049 | 3/1999 |
| WO | 9841562 | 9/1998 |
| WO | 0064486 | 11/2000 |
| WO | 0168066 | 9/2001 |
| WO | 0174402 | 10/2001 |
| WO | 02089789 | 11/2002 |

(Continued)

OTHER PUBLICATIONS

International Search Report and Written Opinion dated Aug. 13, 2008 issued in PCT/US07/03808.
Greenwald, R. B., et al., Camptothecin-20-PEG ester Transport Forms: the Effect of . . . , Bioorganic & Medicinal Chemistry, 6: 551-562, 1998.
Conover, C. D., et al., Camptothecin delivery systems: the utility of amino acid spacers for . . . , Anticancer Drug Design, 14: 499-506, 1999.
Carpino, L.A., et al., New family of base- and nucleophile-sensitive amino-protecting groups. A Michael-acceptor-based deblocking process. Practical utilization of the 1,1 -dioxobenzo[b]thiophene-2-ylmethylcarbonyl (Bsmoc) group, Journal of the American Chemical Society, 119: 9915-9916, 1997.

(Continued)

*Primary Examiner*—Charanjit S Aulakh
(74) *Attorney, Agent, or Firm*—Lucas & Mercanti, LLP

(57) ABSTRACT

A four arm-polyethylene glycol-7-ethyl-10-hydroxycamptothecin conjugate, such as,

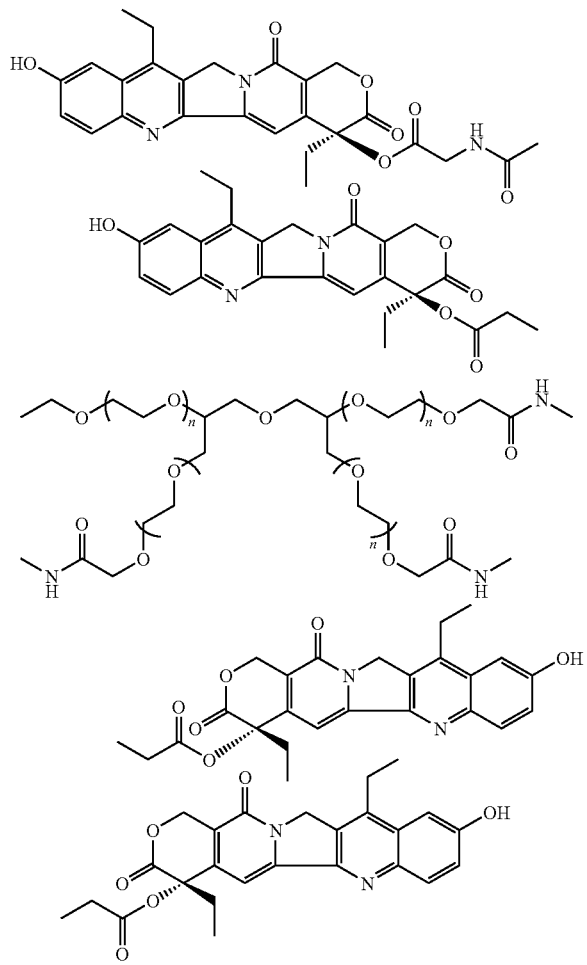

is disclosed. Methods of making the conjugates and methods of treating mammals using the same are also disclosed.

23 Claims, 14 Drawing Sheets

U.S. PATENT DOCUMENTS

| | | | |
|---|---|---|---|
| 5,648,506 | A | 7/1997 | Desai et al. |
| 5,681,567 | A | 10/1997 | Martinez et al. |
| 5,840,900 | A | 11/1998 | Greenwald et al. |
| 5,840,973 | A | 11/1998 | Yasukohchi et al. |
| 5,859,022 | A | 1/1999 | Hausheer et al. |
| 5,880,131 | A | 3/1999 | Greenwald et al. |
| 5,902,588 | A | 5/1999 | Greenwald et al. |
| 5,948,155 | A | 9/1999 | Yui et al. |
| 5,965,566 | A | 10/1999 | Greenwald et al. |
| 6,011,042 | A | 1/2000 | Greenwald et al. |
| 6,111,107 | A | 8/2000 | Greenwald et al. |
| 6,121,451 | A | 9/2000 | Henegar et al. |
| 6,127,355 | A | 10/2000 | Greenwald et al. |
| 6,153,655 | A | 11/2000 | Martinez et al. |
| 6,177,087 | B1 | 1/2001 | Greenwald et al. |
| 6,194,580 | B1 | 2/2001 | Greenwald et al. |
| 6,395,266 | B1 | 5/2002 | Martinez et al. |
| 6,403,569 | B1 | 6/2002 | Achterrath |
| 6,461,603 | B2 | 10/2002 | Bentley et al. |
| 6,608,076 | B1 | 8/2003 | Greenwald et al. |
| 6,638,499 | B2 | 10/2003 | Martinez et al. |
| 6,649,778 | B1 | 11/2003 | Zhao et al. |
| 6,737,505 | B2 | 5/2004 | Bentley et al. |
| 6,756,037 | B2 | 6/2004 | Greenwald et al. |
| 6,875,841 | B2 | 4/2005 | Sakanoue et al. |
| 7,462,627 | B2 * | 12/2008 | Zhao et al. ............... 514/283 |
| 2002/0182172 | A1 | 12/2002 | Bentley et al. |
| 2004/0009229 | A1 | 1/2004 | Unger et al. |
| 2004/0058981 | A1 | 3/2004 | Lai et al. |
| 2004/0077595 | A1 | 4/2004 | Cheng et al. |
| 2004/0247624 | A1 | 12/2004 | Unger et al. |
| 2005/0112088 | A1 | 5/2005 | Zhao et al. |
| 2005/0214250 | A1 | 9/2005 | Harris et al. |
| 2005/0226843 | A1 | 10/2005 | Bentley et al. |
| 2007/0173615 | A1 | 7/2007 | Zhao et al. |
| 2008/0058364 | A1 | 3/2008 | Sapra |
| 2008/0193408 | A1 | 8/2008 | Zhao et al. |

FOREIGN PATENT DOCUMENTS

| | | |
|---|---|---|
| WO | 03031467 | 4/2003 |
| WO | 03037384 | 5/2003 |
| WO | 03037385 | 5/2003 |
| WO | 2004060967 | 7/2004 |

OTHER PUBLICATIONS

Chabot, G. G., Clinical pharmacokinetics or irinotecan, Clinical Pharmacokinet, 33: 245-259, 1997.

Choe, Y. H., et al., Anticancer drug delivery systems: N4-acyl-poly(ethyleneglycol) prodrugs of ara-C. I. Efficacy in solid tumors, Journal of Controlled Release, 79: 41-53, 2002.

Conover, C.D., et al., Camptothecin delivery systems: enhanced efficacy and tumor accumulation of camptothecin following its conjugation to polyethylene glycol via a glycine linker, Cancer Chemotherapy Pharmacology, 407-414, 1998.

Duncan, R., Polymer conjugates as anticancer nanomedicines, Nature Reviews: Cancer, 6: 688-701, 2006.

Garcia-Carbonero, R., et al., Current perspectives on the clinical experience, pharmacology, and continued development of the camptothecins, Clinical Cancer Research, 8: 641-661, 2002.

Gottlieb, J.A., et al., Preliminary pharmacologic and clinical evaluation of camptothecin sodium (NSC-100880), Cancer Chemotherapy Reports, 54: 461-470, 1970.

Greenwald, R. B., et al., Synthesis, isolation, and characterization of 2'-paclitaxel glycinate: an application of the Bsmoc protecting group, Journal of Organic Chemistry, 68: 4894-6, 2003.

Greenwald, R. B., et al., Drug delivery systems. 2. Camptothecin 20-O-poly(ethylene glycol) ester transport forms, Journal of Medicinal Chemistry, 39: 1938-1940, 1996.

Greenwald, R. B., et al., Drug delivery systems: water soluble taxol 2'-poly(ethylene glycol) ester prodrugs—Design and in vivo effectiveness, Journal of Medicinal Chemistry, 39: 424-431, 1996.

Greenwald, R.B., et al., Effective drug delivery by PEGylated drug conjugates, Advanced Drug Delivery Reviews, 55: 217-250, 2003.

Kaneda, N., et al., Metabolism and pharmacokinetics of the camptothecin analogue CPT-11 in the mouse, Cancer Research, 50:1715-1720, 1990.

Kawato, Y., et al., Intracellular roles of SN-38, a metabolite of the camptothecin derivative CPT-11, in the antitumor effect of CPT-11, Cancer Research, 51: 4187-4191, 1991.

Liu, X., et al., Degradation of camptothecin-20(S)-glycinate ester prodrug under physiological conditions, Journal of Pharmaceutical and Biomedical Analysis, 35: 1113-1125, 2004.

Maeda, H., et al., Tumor vascular permeability and the EPR effect in macromolecular therapeutics: a review, Journal of Controlled Release, 65: 271-284, 2000.

Mathijssen, R. H. J., et al., Clinical pharmacokinetics and metabolism of irinotecan (CPT-11), Clinical Cancer Research, 7: 2182-2194, 2001.

Pommier, Y., Topoisomerase I inhibitors: camptothecins and beyond, Nature Reviews: Cancer, 6:789-802, 2006.

Rowinsky, E. K., et al., A Phase I and pharmacokinetic study of pegylated camptothecin as a 1-hour infusion every 3 weeks in patients with advanced solid malignancies, Journal of Clinical Oncology, 148-157, 2003.

Senter, P.D., et al., Identification and activities of human carboxylesterases for the activation of CPT-11, a clinically approved anticancer drug, Bioconjugate Chemisty, 12:1074-1080, 2001.

Slatter, J.G., et al., Bioactivation of the anticancer agent CPT-11 to SN 38 by human hepatic microsomal caarboxylesterases and the in vitro assessment of potential drug interactions, Drug Metabolism and Disposition, 25: 1157-1164, 1997.

Slatter, J. G., et al., Pharmacokinetics, metabolism, and excretion of irinotecan (CPT-11) following i.v. infusion of [14C] CPT-11 in cancer patients, Drug Metabolism and Disposition, 28: 423-433, 2000.

Smith, N.F., et al., Pharmacogenetics of irinotecan metabolism and transport: an update, Toxicology in Vitro, 20: 163-175, 2006.

Ulukan, H., et al., Camptothecins: a review of their chemotherapeutic potential, Drugs, 62:2039-57, 2002.

Zhang, J.A., et al., Development and characterization of a novel liposome-based formulation of SN-38, International Journal of Pharmaceutics, 270: 93-107, 2004.

Zhao, H., et al., 20-O-acylcamptothecin derivatives: evidence for lactone stabilization, Journal of Organic Chemistry, 65: 4601-4606, 2000.

Zalipsky et al. Attachment of Drugs to Polyethylene Glycols, European Polymer Journal, 1983, 19(12): 1177-1183.

Greenwald et al., Poly(ethylene glycol) Conjugated Drugs and Prodrugs: A Comprehensive Review, Critical Review in Therapeutic Drug Carrier Systems, 2000, 17(2): 101-161.

* cited by examiner

MULTI-ARM POLYMERIC CONJUGATES OF 7-ETHYL-10-HYDROXYCAMPTOTHECIN FOR TREATMENT OF BREAST, COLORECTAL, PANCREATIC, OVARIAN AND LUNG CANCERS

CROSS-REFERENCE TO RELATED APPLICATION

This patent application is a continuation of U.S. patent application Ser. No. 11/704,607 filed on Feb. 9, 2007, which claims the benefit of priority from U.S. Provisional Patent Application Ser. Nos. 60/772,464 filed Feb. 9, 2006, 60/804,391 filed Jun. 9, 2006, 60/844,938 filed Sep. 15, 2006 and 60/864,516 filed Nov. 6, 2006, the contents of each of which are incorporated herein by reference.

FIELD OF INVENTION

The present invention relates to multi-arm polymeric pro-drugs of 7-ethyl-10-hydroxycamptothecin. In particular, the invention relates to four-arm polyethylene glycol conjugates of 7-ethyl-10-hydroxycamptothecin and use thereof.

BACKGROUND OF INVENTION

Over the years, several methods of administering biologically-effective materials to mammals have been proposed. Problems arise when the desired medicinal agent is insoluble in aqueous fluids. Alkaloids are often especially difficult to solubilize.

Camptothecin is a water-insoluble cytotoxic alkaloid produced by *Camptotheca accuminata* trees indigenous to China and *Nothapodytes foetida* trees indigenous to India. Camptothecin and related analogs are known to be potential anti-cancer agents and have demonstrated therapeutic activity in vitro and in vivo.

Camptothecin and analogs are known as DNA topoisomerase I inhibitors. For example, one of camptothecin analogs is Irinotecan (CPT-11, Camptosar®) which is also a DNA topoisomerase I inhibitor and has also showed anticancer activity. 7-ethyl-10-hydroxycampothecin is an active metabolite of CPT-11.

SUMMARY OF INVENTION

In order to overcome the above problems and improve the technology for drug delivery through PEGylation, there are provided new methods to directly use multi-armed PEGs to conjugate to drug molecules through proper linkers. In this way, there is no need to incorporate laborious branching moieties to the PEG. In addition, the drug molecules are relatively far from each other. Therefore the conjugation efficiency to the PEG is greatly increased. The solubility of the PEG conjugate is also improved over the end-branched approach.

In one aspect of the invention, compounds of Formula (I) are provided:

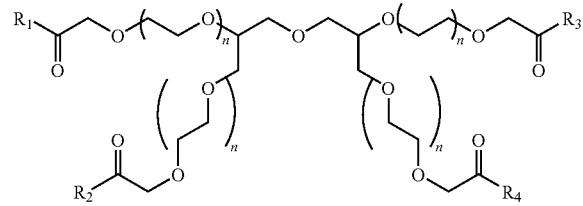

wherein
$R_1$, $R_2$, $R_3$ and $R_4$ are independently OH or $(L)_m$-D;
L is a bifunctional linker;
D is a residue of a camptothecin or a camptothecin analog, such as

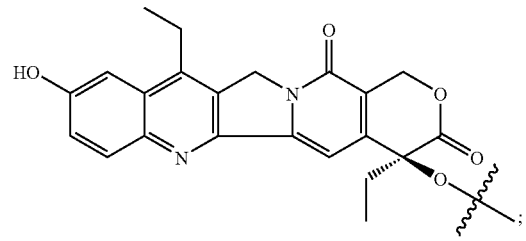

m is 0 or a positive integer; and
n is a positive integer;

provided that $R_1$, $R_2$, $R_3$ and $R_4$ are not all OH.

In this aspect of the invention, the camptothecin or camptothecin analog is reacted with the polymer so that the 20-OH group thereof forms conjugates with the four-arm polymers.

In one preferred aspect of the invention, L is a residue of an amino acid. In certain preferred aspects of the invention, n is from about 28 to about 341, and is preferably about 227.

Methods of making the conjugates as well as methods of treatment using the compounds of the present invention are also provided.

Advantages will be apparent from the following description and drawings.

For purposes of the present invention, the term "residue" shall be understood to mean that portion of a compound, to which it refers, i.e. camptothecin analog, 7-ethyl-10-hydroxycamptothecin, amino acid, etc. that remains after it has undergone a substitution reaction with another compound.

For purposes of the present invention, the term "polymeric containing residue" or "PEG residue" shall each be understood to mean that portion of the polymer or PEG which remains after it has undergone a reaction with camptothecin or camptothecin analog-containing compounds.

For purposes of the present invention, the term "alkyl" shall be understood to include straight, branched, substituted, e.g. halo-, alkoxy-, nitro-, $C_{1-12}$, but preferably $C_{1-4}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mereaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitro-phenoxy. Halo shall be understood to include fluoro, chloro, iodo and bromo.

The terms "effective amounts" and "sufficient amounts" for purposes of the present invention shall mean an amount which achieves a desired effect or therapeutic effect as such effect is understood by those of ordinary skill in the art.

DETAILED DESCRIPTION OF INVENTION

Figure 1:
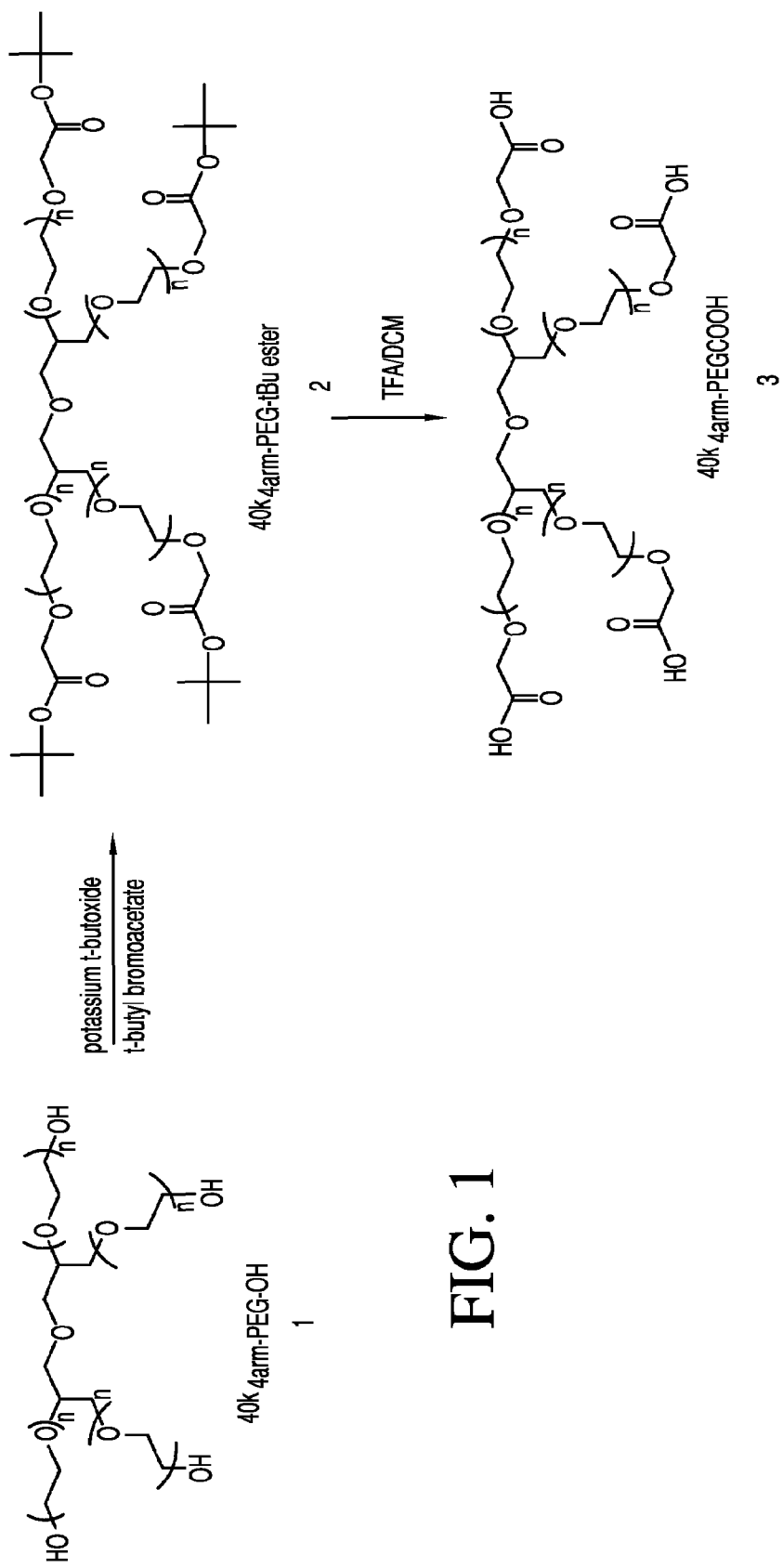
FIG. 1 schematically illustrates a reaction scheme of preparing four-arm polyethylene glycol acids.
Figure 2:
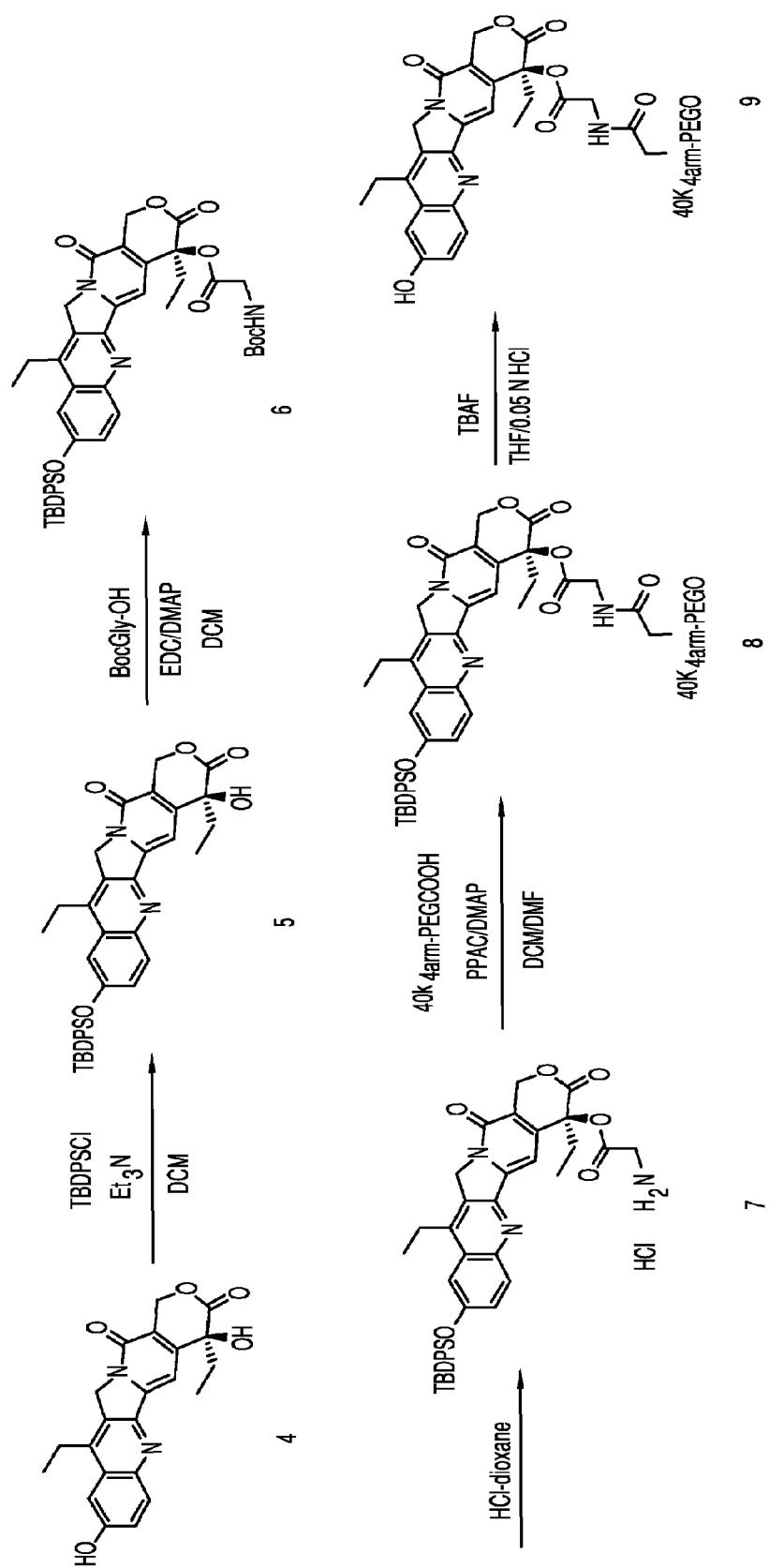
FIG. 2 schematically illustrates a reaction scheme of preparing 4arm-PEG-Gly-(7-ethyl-10-hydroxycamptothecin) described in Examples 3-7.
Figure 3:
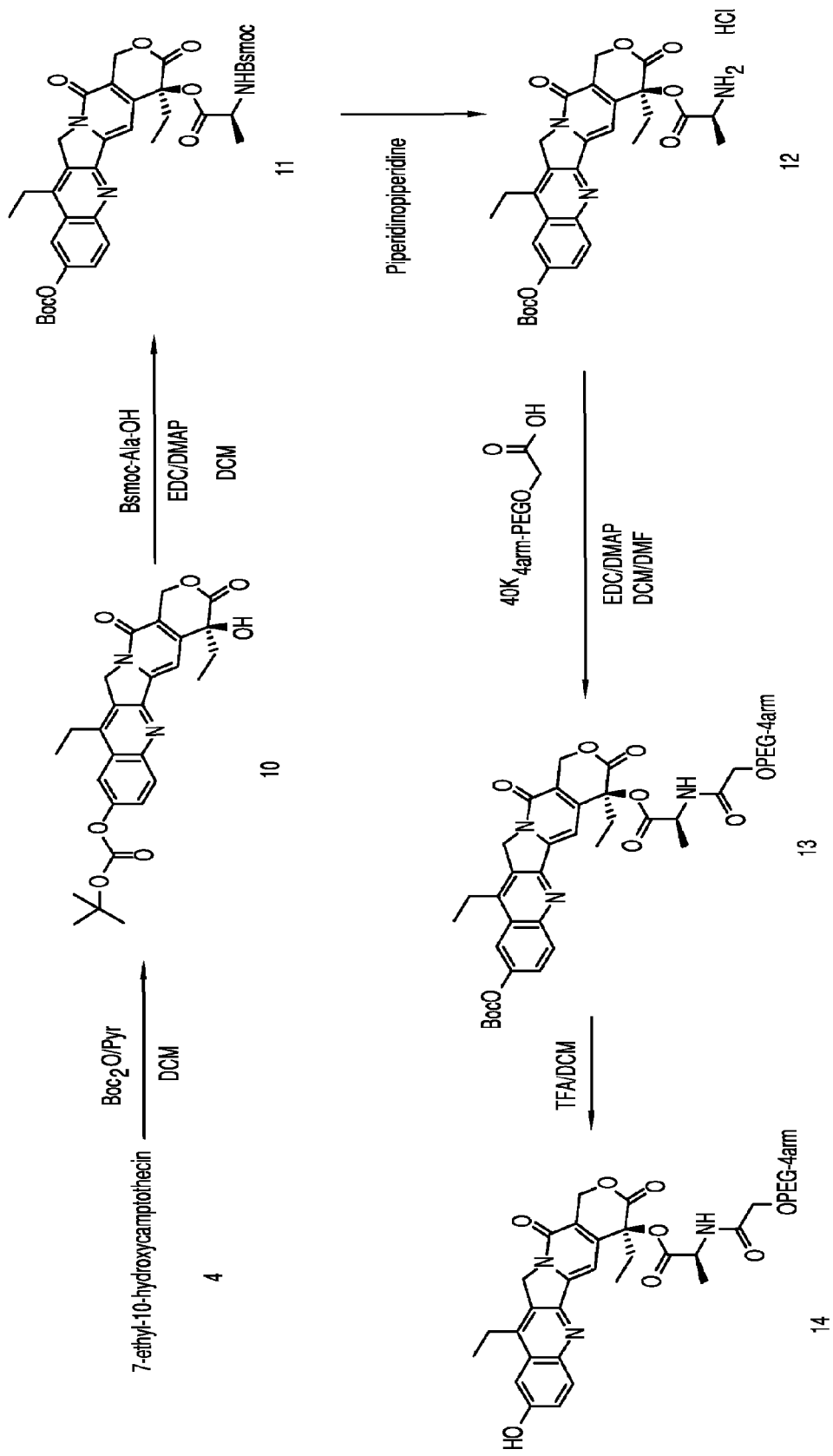
FIG. 3 schematically illustrates a reaction scheme of preparing 4arm-PEG-Ala-(7-ethyl-10-hydroxycamptothecin) described in Examples 8-12.
Figure 4:
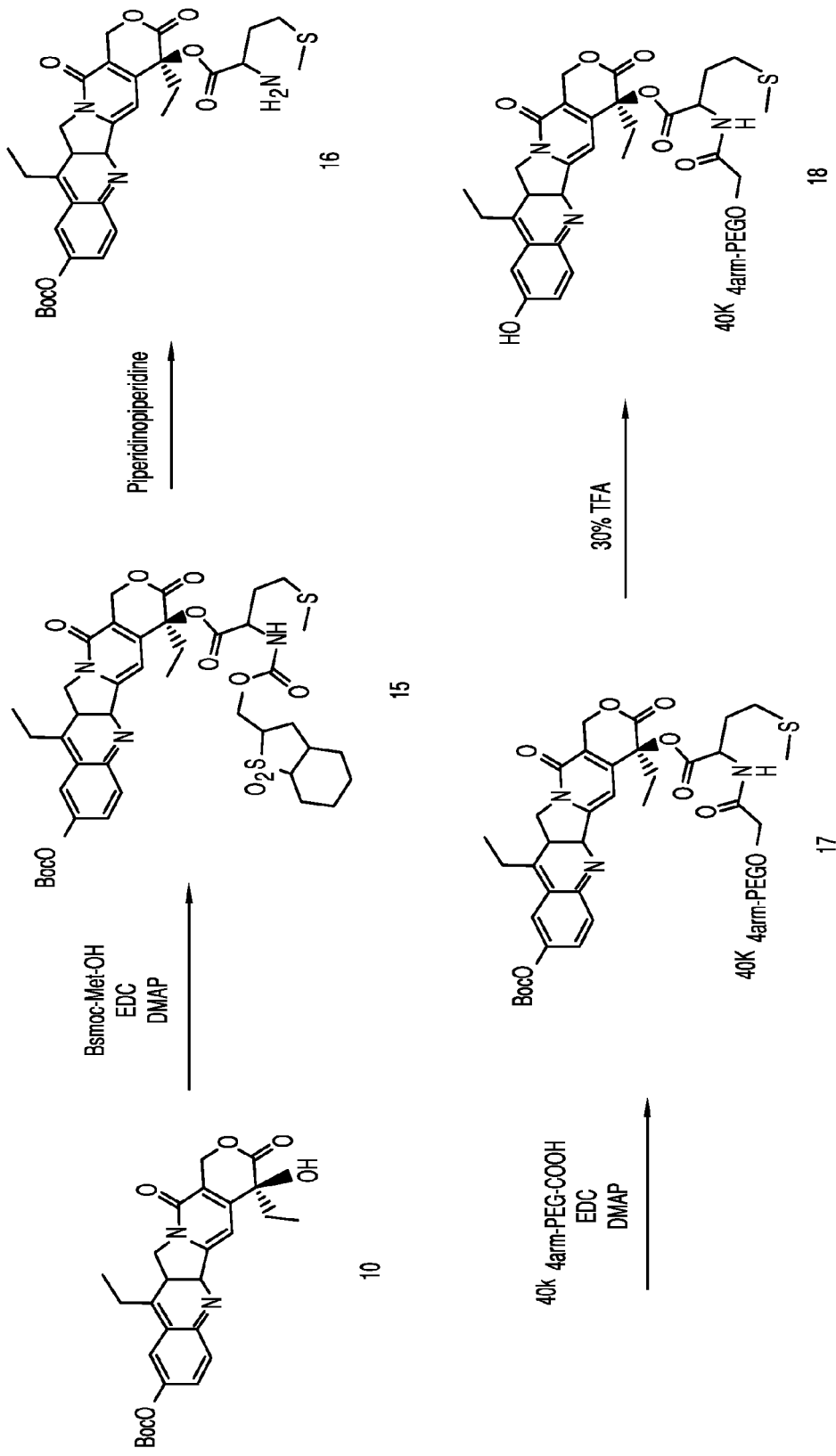
FIG. 4 schematically illustrates a reaction scheme of preparing 4arm-PEG-Met-(7-ethyl-10-hydroxycamptothecin) described in Examples 13-16.
Figure 5:
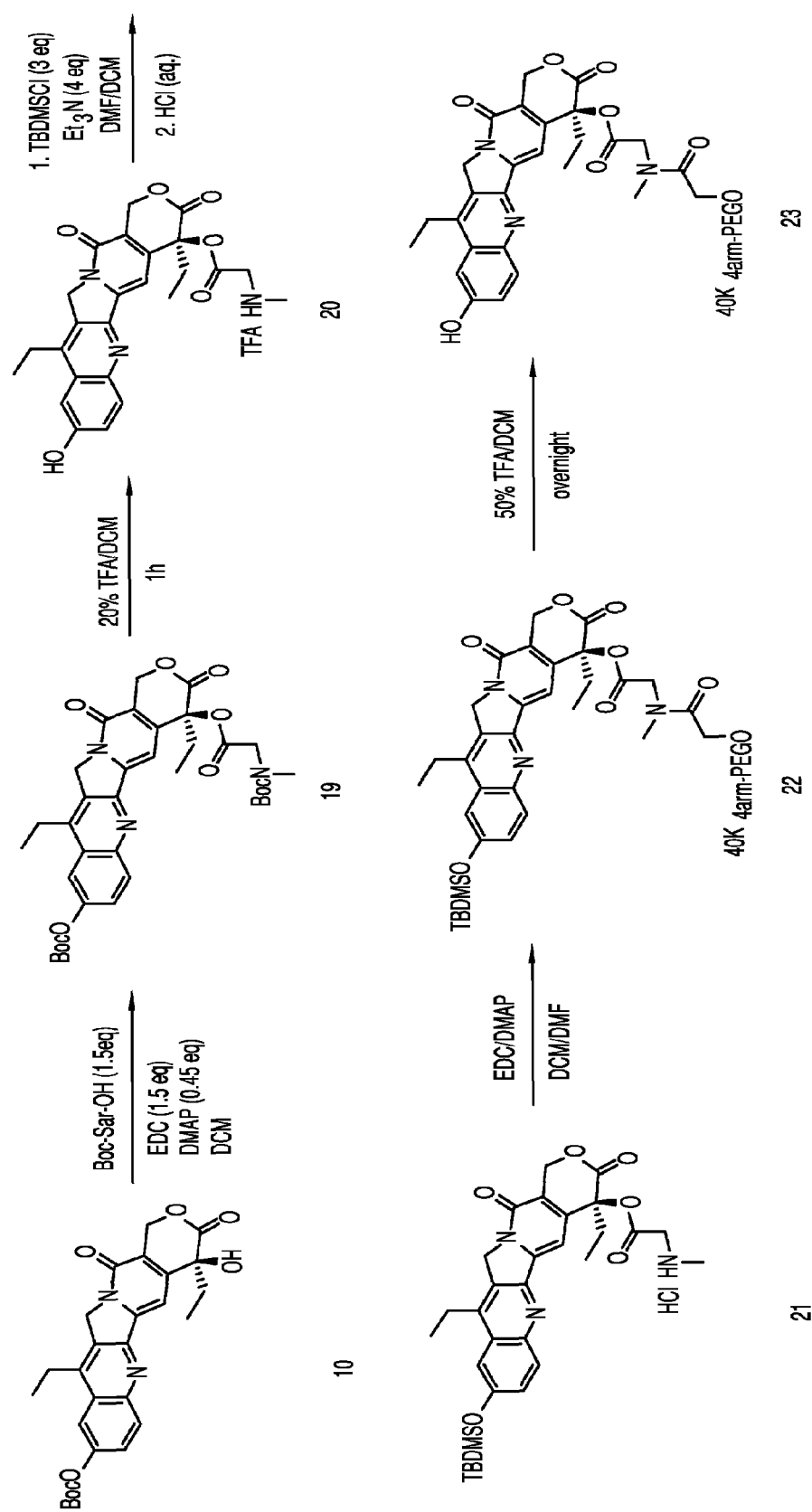
FIG. 5 schematically illustrates a reaction scheme of preparing 4arm-PEG-Sar-(7-ethyl-10-hydroxycamptothecin) described in Examples 17-21.

In one embodiment of the present invention, there are provided compounds of Formula (I):

wherein
$R_1$, $R_2$, $R_3$ and $R_4$ are independently OH or $(L)_m$-D;
L is a bifunctional linker;

D is a residue of a camptothecin or a camptothecin analog, such as m is 0 or a positive integer preferably from about 1 to about 10, and more preferably 1; and n is a positive integer, preferably from about 28 to about 341, more preferably about 227;

provided that $R_1$, $R_2$, $R_3$ and $R_4$ are not all OH.

A. Camptothecin and Related Camptothecin Analogs

Camptothecin is a water-insoluble cytotoxic alkaloid produced by *camptoteca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo in laboratory animals.

Camptothecin and certain related analogues share the structure:

From this core structure, several known analogs have been prepared. For example, the A ring in either or both of the 10- and 11-positions can be substituted with an OH. The A ring can also be substituted with a straight or branched $C_{1-30}$ alkyl or $C_{1-17}$ alkoxy, optionally linked to the ring by a heteroatom i.e. —O or —S. The B ring can be substituted in the 7-position with a straight or branched $C_{1-30}$ alkyl (preferably $C_2$ alkyl), $C_{5-8}$ cycloakyl, $C_{1-30}$ alkoxy, phenyl alkyl, etc., alkyl carbamate, alkyl carbazides, phenyl hydrazine derivatives, etc. Other substitutions are possible in the C, D and E rings. See, for example, U.S. Pat. Nos. 5,004,758; 4,943,579; RE 32,518, the contents of which are incorporated herein by reference. As the artisan will appreciate, the 10-hydroxycamptothecin, 11-hydroxycamptothecin and the 10,11-dihydroxycamtothecin analogs occur naturally as one of the minor components in *C. Acuminata* and its relatives. Additional substitutions to these compounds, i.e. 7-alkyl-, 7-substituted alkyl-, 7-amino-, 7-aminoalkyl-, 7-aralkyl-, 9-alkyl-, 9-aralkyl-camptothecin etc. derviatives can be made using known synthetic techniques without undue experimentation. Some camptotheca alkaloids have the structure shown below:

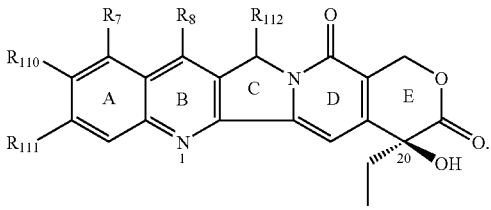

(II)

In the structure shown above, $R_7$ is one of $NO_2$, $NH_2$, $N_3$, hydrogen, halogen (F, Cl, Br, I), COOH, OH, O—$C_{1-8}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$alkyl), O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(CH_2CH_2OH)_2$, O—, NH— and S—$CH_2CH_2N(CH_2CH_2CH_2OH_2)_2$, O—, NH— and S—$CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl.

$R_8$ in the structure (II) shown above can be H or $C_{1-8}$ alkyl (preferably $C_2$ alkyl) or $CH_2NR_9R_{10}$ where (a) $R_9$ and $R_{10}$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl; alternatively (b) $R_9$ can be hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl and $R_{10}$ can be —$COR_{11}$ where $R_{11}$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl; or (c) $R_9$ and $R_{10}$ taken together with the nitrogen atom to which they are attached form a saturated 3-7 membered heterocyclic ring which may contain a O, S or $NR_{12}$ group, where $R_{12}$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_{13}$ where $R_{13}$ is hydrogen, $C_{1-6}$ alkyl, perhalo-$C_{1-6}$ alkyl, $C_{1-6}$ alkoxy, aryl, and aryl substituted with one or more of $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R_{110}$-$R_{111}$ are each independently selected from the group consisting of hydrogen; halo; acyl; alkyl (e.g., $C_{1-6}$ alkyl); substituted alkyl; alkoxy (e.g., $C_{1-6}$ alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —$C(R_{117})$=N—$(O)_j$—$R_{118}$ wherein $R_{117}$ is H, alkyl, alkenyl, cycloalkyl, or aryl, j is 0 or 1, and $R_{118}$ is H, alkyl, alkenyl, cycloalkyl, or heterocycle; and $R_{119}$—(O)O— wherein $R_{119}$ is halogen, amino, substituted amino, heterocycle, substituted heterocycle, or $R_{120}$—O—$(CH_2)_k$— where k is an integer of 1-10 and $R_{120}$ is alkyl, phenyl, substituted phenyl, cycloalkyl, substituted cycloalkyl, heterocycle, or substituted heterocycle; or $R_7$ together with $R_{110}$ or $R_{110}$ together with $R_{111}$ form substituted or unsubstituted methylenedioxy, ethylenedioxy, or ethyleneoxy; and $R_{112}$ is H or OR', wherein R' is alkyl, alkenyl, cycloalkyl, haloalkyl, or hydroxyalkyl.

Preferred aryl groups are phenyl and naphthyl. Suitable heterocyclic rings when $R_9$ and $R_{10}$ are taken together with the nitrogen atom to which they are attached include: aziridine, azetidine, pyrrolidine, piperidine, hexamethylenimine, imidazolidine, pyrazolidine, isoxazolidine, piperazine, N-methylpiperazine, tetrahydroazepine, N-methyl-tetrahydroazepine, thiazolidine, etc. After conjugation, the remaining camptothecin analog is referred to as the residue of the unconjugated compound.

For ease of description and not limitation, the description refers to 7-ethyl-10-hydroxycamptothecin as the camptothecin analog as the preferred and illustrated compound. It will be understood that the claimed invention includes all such derivatives and analogs so long as the analog has an OH such as the 20-OH group for the point of attachment to the polymer. The camptothecin or camptothecin analogs can be racemic mixtures or optically pure isomer. Preferably, a substantially pure and active form of such as the 20(S) camptothecin or camptothecin analog is employed in the multi-arm polymeric prodrugs.

B. Bifunctional Linkers

In certain preferred aspects of the present invention, L is a residue of an amino acid. The amino acid which can be selected from any of the known naturally-occurring L-amino acids is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. In alternative aspects, L can be a peptide residue. The peptide can range in size, for instance, from about 2 to about 10 amino acid residues.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include:

2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine or sarcosine, N-methyl-isoleucine, 6-N-methyllysine, N-methylvaline, norvaline, norleucine, ornithine, and others too numerous to mention, that are listed in 63 Fed. Reg., 29620, 29622, incorporated by reference herein. Some preferred L groups include glycine, alanine, methionine or sarcosine residues. More preferably, compounds of the present invention include a glycine residue as the Tinker group (L).

In another aspect of the present invention, L after attachment between the camptothecin analog and polymer is selected among:

—$[C(O)]_vNR_{21}(CR_{22}R_{23}O)_t$—,
—$[C(O)]_vNR_{21}(CR_{22}R_{23}O)_t(CR_{24}R_{25})_yO$—,
—$[C(O)]_vNR_{21}(CR_{22}R_{23}O)_t(CR_{24}R_{25})_y$—,
—$[C(O)]_vNR_{21}(CR_{22}R_{23})_tO$—,
—$[C(O)]_vNR_{21}(CR_{22}R_{23})_t(CR_{24}CR_{25}O)_yNR_{26}$—,
—$[C(O)]_vO(CR_{22}R_{23})_tNR_{26}$—,
—$[C(O)]_vO(CR_{22}R_{23})_tO$—,
—$[C(O)]_vNR_{21}(CR_{22}R_{23})_tNR_{26}$—,

—[C(O)]$_v$NR$_{21}$(CR$_{22}$R$_{23}$)$_t$(CR$_{24}$CR$_{25}$O)$_y$—,
—[C(O)]$_v$NR$_{21}$(CR$_{22}$R$_{23}$O)$_t$(CR$_{24}$CR$_{25}$)$_y$NR$_{26}$—,

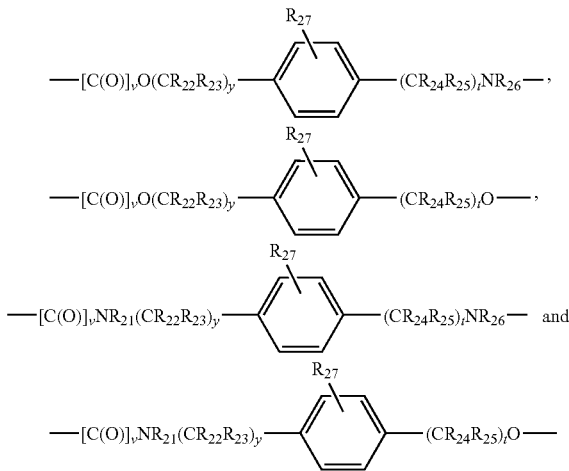

wherein:

$R_{21}$-$R_{26}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{27}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, NO$_2$, haloalkyl and halogen;

t and y are individually selected positive integers from about 1 to about 4; and v is 0 or 1.

In some preferred aspects of the present invention, the compounds include one unit of the bifunctional linker and thus m is 1.

Additional linkers are found in Table 1 of Greenwald et al. (*Bioorganic & Medicinal Chemistry*, 1998, 6:551-562), the contents of which are incorporated by reference herein.

C. Multi-Arm Polymers

Multi-arm PEG's are those described in NOF Corp. Drug Delivery System catalog, Ver. 8, April 2006, the disclosure of which is incorporated herein by reference. One particularly preferred multi-arm PEG has the structure:

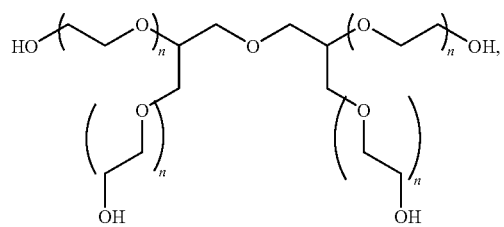

wherein n is a positive integer.

In one preferred embodiment of the invention, the degree of polymerization for the polymer (n) is from about 28 to about 341 to provide polymers having a total molecular weight of from about 5,000 Da to about 60,000 Da, and preferably from about 114 to about 227 to provide polymers having a total molecular weight of from 20,000 Da to 40,000 Da. This represents the number of repeating units in the polymer chain and is dependent on the molecular weight of the polymer. In one particularly preferred embodiment of the invention, n is about 227.

D. Synthesis of Prodrugs

Generally, the prodrugs of the invention are prepared by reacting one or more equivalents of an activated multi-arm polymer with, for example, one or more equivalents per active site of camptothecin-amino acid conjugate under conditions which are sufficient to effectively cause the amino group to undergo a reaction with the carboxylic acid of the polymer and form a linkage.

More specifically, the methods can include:

1) providing one equivalent of a camptothecin or camptothecin analog containing an available 20-hydroxyl group and one or more equivalents of a bifunctional linker containing an available carboxylic acid group;

2) reacting the two reactants to form a camptothecin-bifunctional linker intermediate in an inert solvent such as DCM (or DMF, chloroform, toluene or mixtures thereof) in the presence of a coupling reagent such as 1,(3-dimethyl aminopropyl) 3-ethyl carbodiimide (EDC), (or 1,3-diisopropylcarbodiimide (DIPC), any suitable dialkyl carbodiimide, Mukaiyama reagents, (e.g. 2-halo-1-alkyl-pyridinium halides) or propane phosphonic acid cyclic anhydride (PPACA), etc) and a suitable base such as DMAP; and 3) reacting one or more equivalents per active site (2 eq. in Example) of the resulting intermediate having an amine group and one equivalent of an activated polymer, such as a PEG-acid in an inert solvent such as DCM (or DMF, chloroform, toluene or mixtures thereof) in the presence of a coupling reagent such as 1,(3-dimethyl aminopropyl) 3-ethyl carbodiimide (EDC), PPAC (or 1,3-diisopropylcarbodiimide (DIPC), any suitable dialkyl carbodiimide; Mukaiyama reagents, (e.g. 2-halo-1-alkyl-pyridinium halides) or propane phosphonic acid cyclic anhydride (PPACA), etc.), and a suitable base such as DMAP, which are available, for example, from commercial sources such as Sigma Chemical, or synthesized using known techniques, at a temperature from 0EC up to 22EC.

In one preferred aspect, the 10-hydroyl group of 7-ethyl-10-hydroxycamptothecin is protected prior to step 1).

Aromatic protecting groups for the OH group of camptothecin or camptothecin analog such as 10-hydroxyl group in 7-ethyl-10-hydroxycamptothecin are preferred because 7-ethyl-10-hydroxycamptothecin intermediates thereof have better solubility and can be purified in highly pure form efficiently and effectively. For example, silyl-containing protecting groups such as TBDPSCl, TBDMSCl and TMSCl can be used to protect the 10-hydroxyl group in camptothecin or camptothecin analog.

The activated polymer, i.e., a polymer containing 1-4 terminal carboxyl acid groups can be prepared, for example, by converting NOF Sunbright-type or other branched polymers having terminal OH groups into the corresponding carboxyl acid derivatives using standard techniques well known to those of ordinary skill. See, for example, Examples 1-2 herein as well as commonly assigned U.S. Pat. No. 5,605,976, the contents of which are incorporated herein by reference.

The first and second coupling agents can be the same or different.
Examples of preferred bifunctional linker groups include glycine, alanine, methionine, sarcosine, etc. and syntheses are shown in the Examples. Alternative and specific syntheses are provided in the examples.
For example, the compounds of the present invention are among:
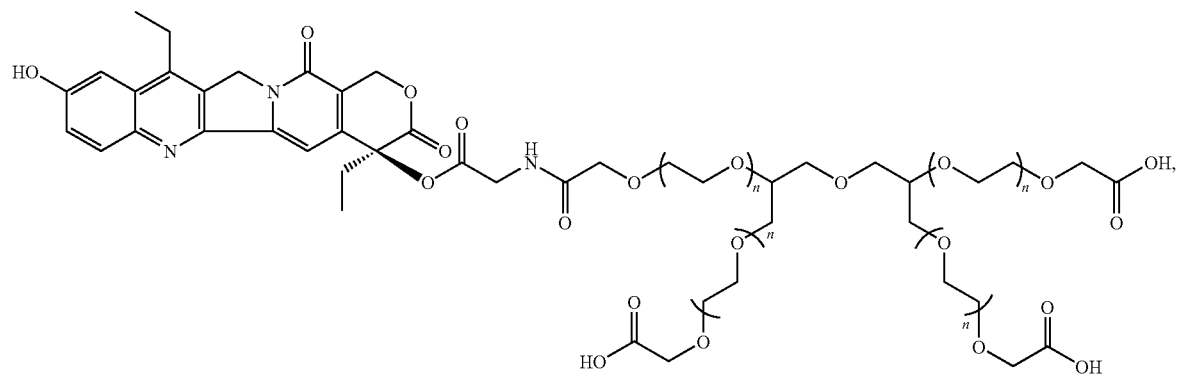
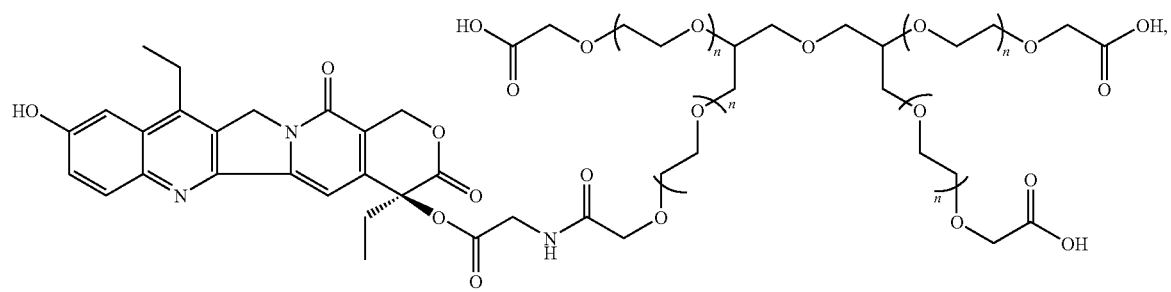
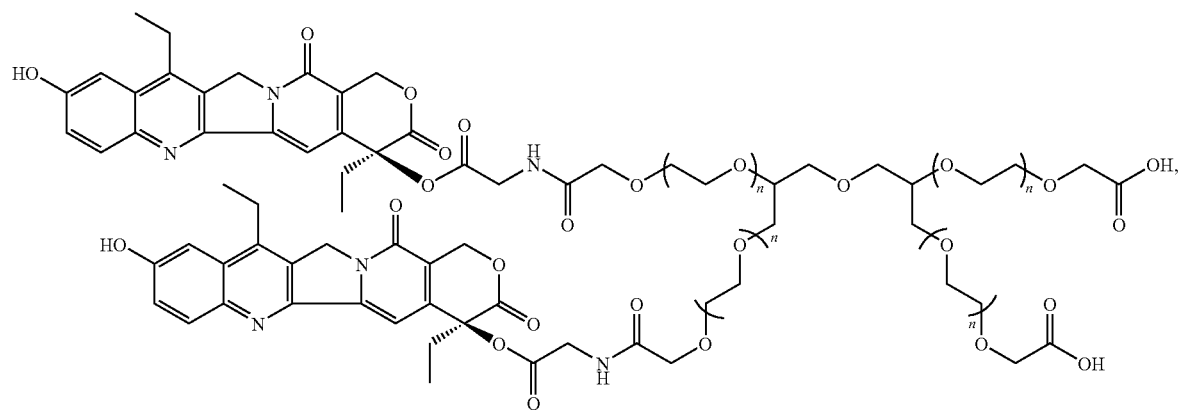
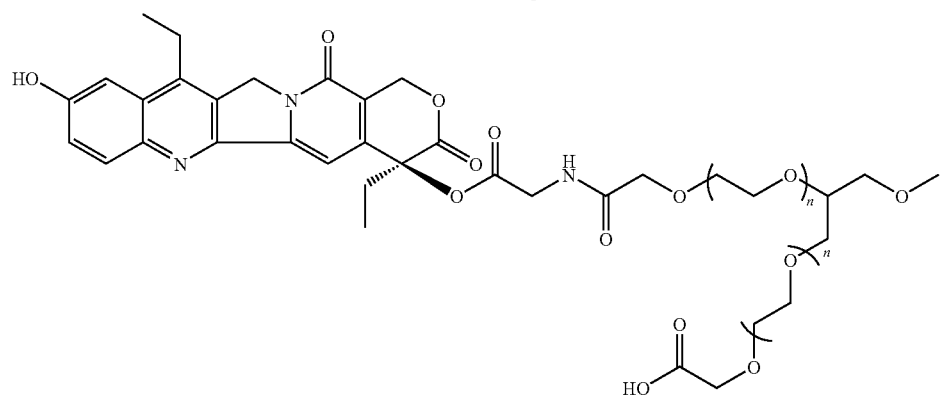

-continued
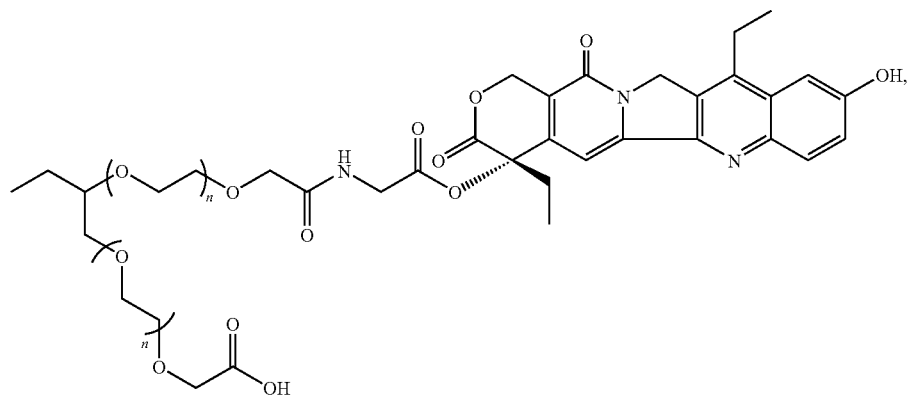
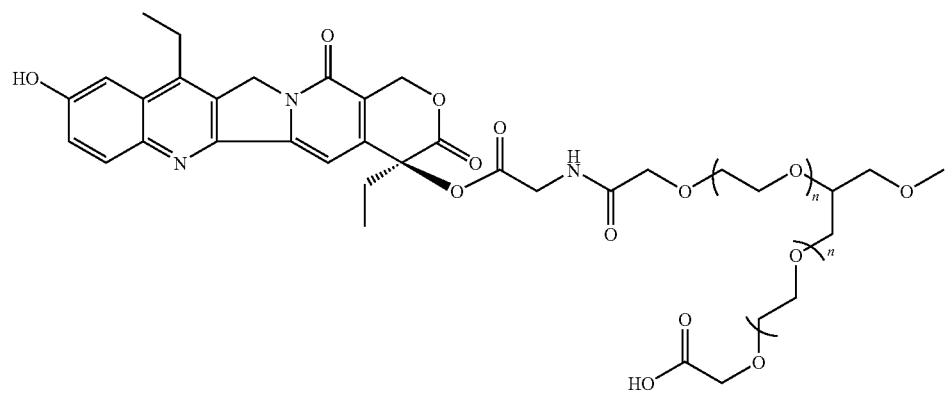
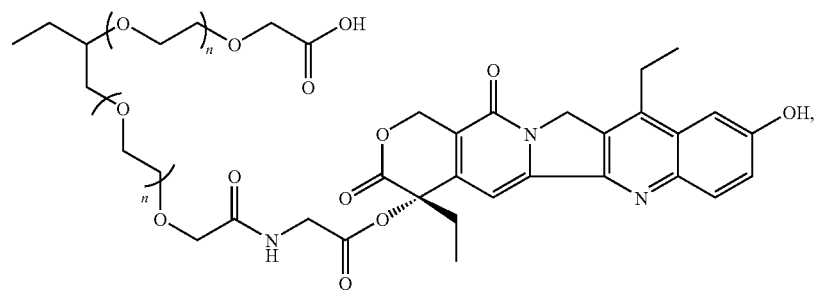
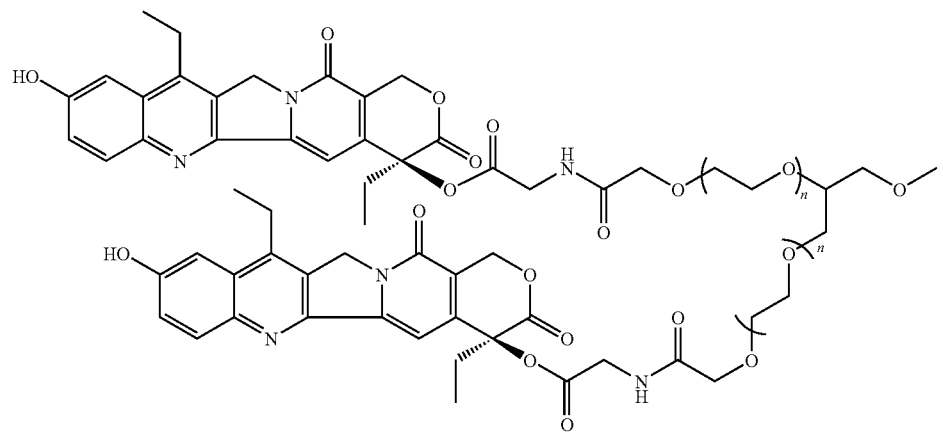

-continued
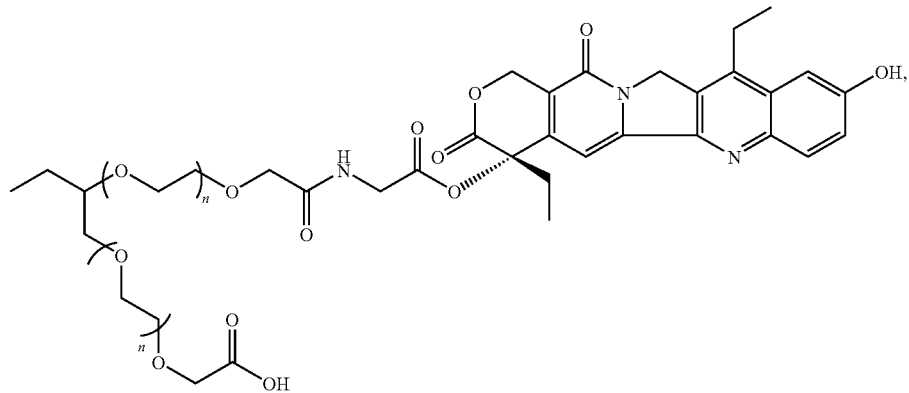
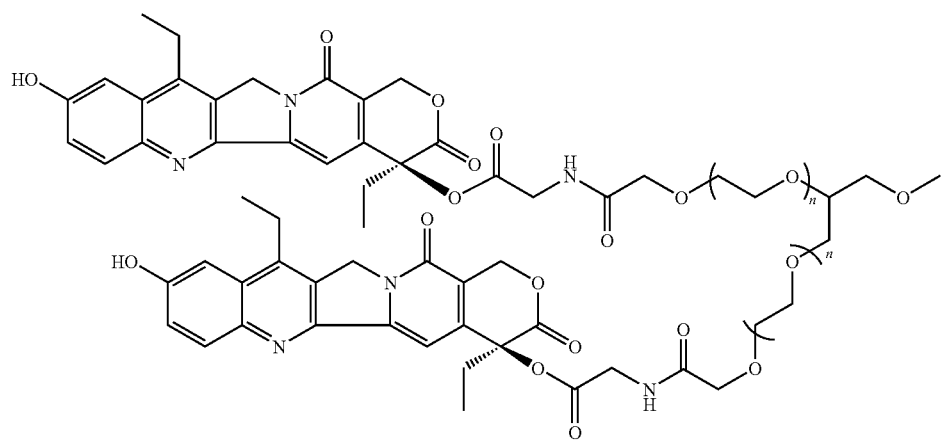
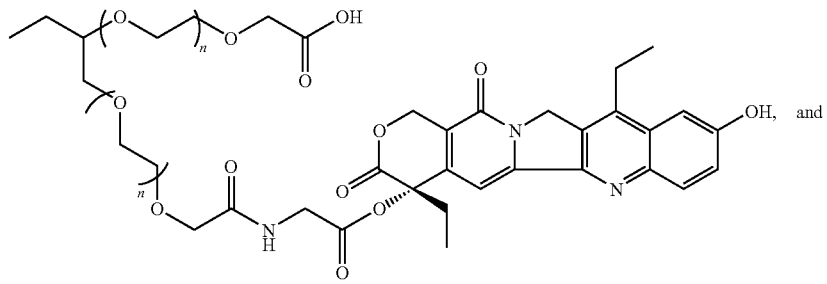
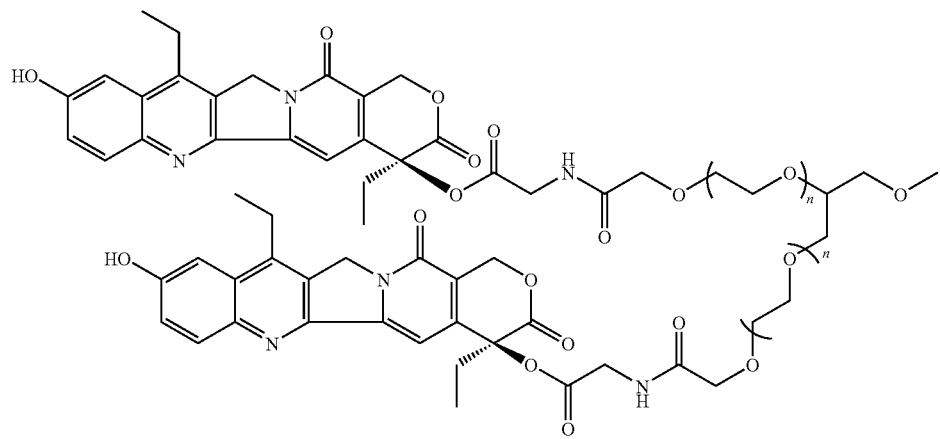

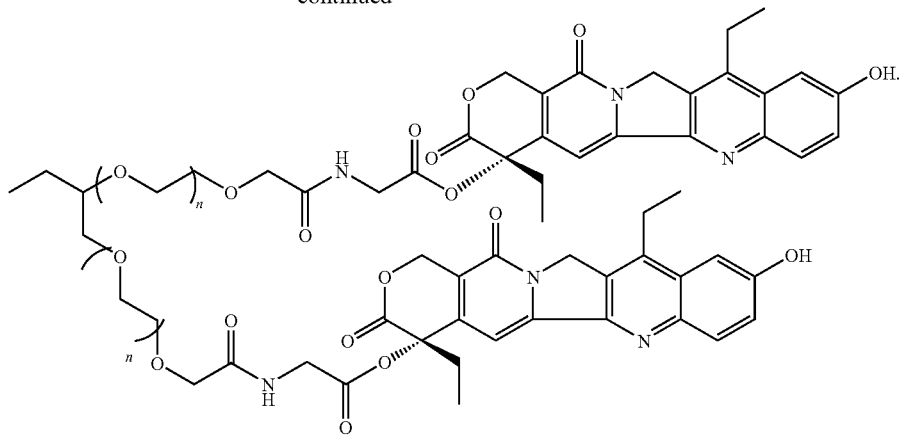

One particularly preferred compound is

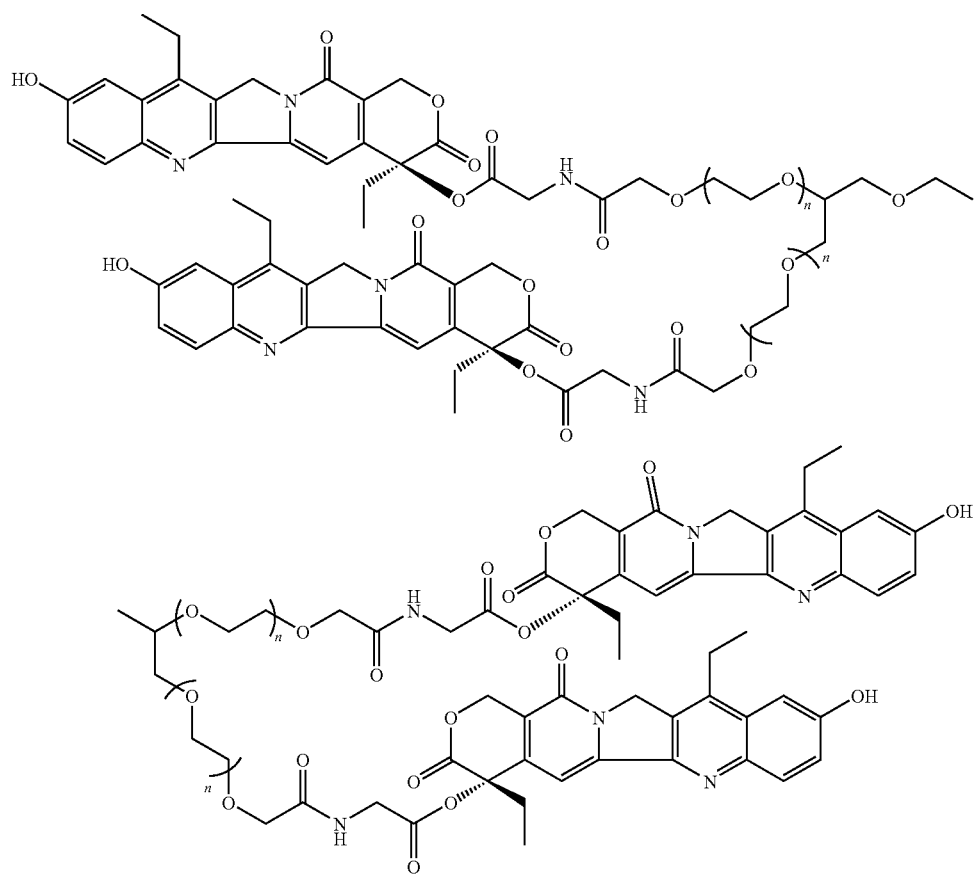

wherein all four arms of the polymer are conjugated to 7-ethyl-10-hydroxycamptothecin through glycine. HPLC analysis of compounds made in accordance with this aspect of the inventions shows that on average, four 7-ethyl-10-hydroxycamptothecin molecules are conjugated to one PEG molecule (4% by weight).

E. Compositions/Formulations

Pharmaceutical compositions containing the polymer conjugates of the present invention may be manufactured by processes well known in the art, e.g., using a variety of well-known mixing, dissolving, granulating, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen. Parenteral routes are preferred in many aspects of the invention.

For injection, including, without limitation, intravenous, intramuscular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

The compounds may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt (preferred) of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the compounds of the present invention can conveniently be delivered in the form of an aerosol spray using a pressurized pack or a nebulizer and a suitable propellant.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems such as liposomes and emulsions can also be used.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

F. Dosages

A therapeutically effective amount refers to an amount of compound effective to prevent, alleviate or ameliorate the camptothecin or related analog, i.e., 7-ethyl-10-hydroxy-camptothecin-susceptible condition. Determination of a therapeutically effective amount is well within the capability of those skilled in the art, especially in light of the disclosure herein.

For any compound used in the methods of the invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients.

Toxicity and therapeutic efficacy of the compounds described herein can be determined by standard pharmaceutical procedures in cell cultures or experimental animals using methods well-known in the art. The dosage, of course, can vary depending upon the dosage form and route of administration. The exact formulation, route of administration and dosage can be selected by the individual physician in view of the patient's condition. In general, however, the presently preferred dosage range for systemic delivery of a compound of this invention will be from about 1 to about 100 mg/kg/week and is preferably from about 2 to about 60 mg/kg/week.

The compositions may be administered once daily or divided into multiple doses which can be given as part of a multi-week treatment protocol. The precise dose will depend on the stage and severity of the condition, the susceptibility of the tumor to the polymer-prodrug composition, and the individual characteristics of the patient being treated, as will be appreciated by one of ordinary skill in the art.

G. Methods of Treatment

In view of the above, there are also provided methods of treating a mammal, comprising administering an effective amount of a compound of the present invention of Formula (I), wherein D is a biologically active moiety, i.e., camptothecin analog to a patient in need thereof. In one preferred aspect of the invention, D is a residue of 7-ethyl-10-hydroxy-camptothecin.

Another aspect of the present invention provides methods of treatment for various medical conditions in mammals. The compositions are useful for, among other things, treating neoplastic disease, reducing tumor burden, preventing metastasis of neoplasms and preventing recurrences of tumor/neoplastic growths in mammals. In alternative aspects, the cancer being treated can be one or more of the following: solid tumors, lymphomas, small cell lung cancer, acute lymphocytic leukemia (ALL), pancreatic cancer, glioblastoma, ovarian cancer, gastric cancers, etc.

The amount of the composition, e.g., used as a prodrug, that is administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, polymeric ester derivatives of camptothecin and related compositions are administered in amounts ranging from about 1 to about 100 mg/kg/week and preferably from about 2 to about 60 mg/kg/week. The range set forth above is illustrative and those skilled in the art will determine the optimal dosing of the prodrug selected based on clinical experience and the treatment indication.

In alternative aspects of the invention, the methods of treatment include administering an effective amount of the compounds described herein to a mammal or patient in need thereof suffering from conditions which can be treated by topoisomerase interference.

EXAMPLES

The following examples serve to provide further appreciation of the invention but are not meant in any way to restrict the effective scope of the invention. The underlined and bold-faced numbers recited in the Examples correspond to those shown in the FIGS. 1-5.

General Procedures. All reactions were run under an atmosphere of dry nitrogen or argon. Commercial reagents were used without further purification. All PEG compounds were dried under vacuum or by azeotropic distillation from toluene prior to use. $^{13}C$ NMR spectra were obtained at 75.46 MHz using a Varian Mercury®300 NMR spectrometer and deuterated chloroform and methanol as the solvents unless otherwise specified. Chemical shifts ($\delta$) are reported in parts per million ppm) downfield from tetramethylsilane (TMS).

HPLC Method. The reaction mixtures and the purity of intermediates and final products were monitored by a Beckman Coulter System Gold® HPLC instrument. It employs a ZOBAX® 300SB C8 reversed phase column (150×4.6 mm) or a Phenomenex Jupiter® 300A C18 reversed phase column (150×4.6 mm) with a multiwavelength UV detector, using a gradient of 10-90% of acetonitrile in 0.05% trifluoroacetic acid (TFA) at a flow rate of 1 mL/min.)

Example 1

$^{40k}$4arm-PEG-tBu Ester (Compound 2)

$^{40k}$4arm-PEG-OH (12.5 g, 1 eq.) was azeotroped with 220 mL of toluene to remove 35 mL of toluene/water. The solution was cooled to 30° C. and 1.0 M potassium t-butoxide in t-butanol (3.75 mL, 3 eq×4=12 eq.) was added. The mixture was stirred at 30° C. for 30 min and then t-butyl bromoacetate (0.975 g, 4 eq.×4=16 eq.) was added. The reaction was kept at 30° C. for 1 hour and then was cooled to 25° C. 150 mL of ether was slowly added to precipitate product. The resulting suspension was cooled to 17° C. and stayed at 17° C. for half hour. The crude product was filtered and the wet cake was washed with ether twice (2×125 mL). The isolated wet cake was dissolved in 50 ml of DCM and the product was precipitated with 350 ml of ether and filtered. The wet cake was washed with ether twice (2×125 mL). The product was dried under vacuum at 40° C. (yield=98%, 12.25 g). $^{13}C$ NMR (75.4 MHz, CDCl$_3$): $\delta$ 27.71, 68.48-70.71 (PEG), 80.94, 168.97.

Example 2

$^{40k}$4arm-PEG Acid (Compound 3)

$^{40k}$4arm-PEG-tBu ester (compound 2, 12 g) was dissolved in 120 mL of DCM and then 60 mL of TFA were added. The mixture was stirred at room temperature for 3 hours and then the solvent was removed under vacuum at 35° C. The resulting oil residue was dissolved in 37.5 mL of DCM. The crude product was precipitated with 375 mL of ether. The wet cake was dissolved in 30 mL of 0.5% NaHCO$_3$. The product was extracted with DCM twice (2×150 ml). The combined organic layers were dried over 2.5 g of MgSO$_4$. The solvent was removed under vacuum at room temperature. The resulting residue was dissolved in 37.5 mL of DCM and the product was precipitated with 300 mL of ether and filtered. The wet cake was washed with ether twice (2×125 ml). The product was dried under vacuum at 40° C. (yield=90%, 10.75 g). $^{13}C$ NMR (75.4 MHz, CDCl$_3$): $\delta$ 67.93-71.6 (PEG), 170.83.

Example 3

TBDPS-(10)-(7-ethyl-10-hydroxycamptothecin) (Compound 5)

To a suspension of 7-ethyl-10-hydroxycamptothecin (compound 4, 2.0 g, 5.10 mmol, 1 eq.) in 100 mL of anhydrous DCM were added Et$_3$N (4.3 mL, 30.58 mmol, 6 eq.) and TBDPSCl (7.8 mL, 30.58 mmol, 6 eq.). The reaction mixture was heated to reflux overnight and then, was washed with a 0.2 N HCl solution (2×50 mL), a saturated NaHCO$_3$ solution (100 mL) and brine (100 mL). The organic layer was dried over MgSO$_4$, filtered and evaporated under vacuum. The residue was dissolved in anhydrous DCM and precipitated by addition of hexanes. The precipitation with DCM/hexanes was repeated to get rid of excess TBDPSCl. The solids were filtered and dried under vacuum to give 2.09 g of product. (65% yield). $^1H$ NMR (300 MHz, CDCl$_3$): $\delta$ 0.90 (3H, t, J=7.6 Hz), 1.01 (3H, t, J=7.3 Hz), 1.17 (9H, s), 1.83-1.92 (2H, m), 2.64 (2H, q, 6.9 Hz), 3.89 (1H, s, OH), 5.11 (2H, s), 5.27 (1H, d, J=16.1 Hz), 5.72 (1H, d, J=16.4 Hz), 7.07 (2H, d, J=2.63 Hz), 7.36-7.49 (7H, m), 7.58 (1H, s), 7.75-7.79 (4H, m), 8.05 (1H, d, J=9.4 Hz). $^{13}C$ NMR (75.4 MHz, CDCl$_3$): $\delta$ 7.82, 13.28, 19.52, 22.86, 26.48, 31.52, 49.23, 66.25, 72.69, 97.25, 110.09, 117.57, 125.67, 126.57, 127.65, 127.81, 130.02, 131.69, 131.97, 135.26, 143.51, 145.05, 147.12, 149.55, 149.92, 154.73, 157.43, 173.72.

Example 4

TBDPS-(10)-(7-ethyl-10-hydroxycamptothecin)-(20)-Gly-Boe (Compound 6)

To a 0° C. solution of TBDPS-(10)-(7-ethyl-10-hydroxycamptothecin) (compound 5, 3.78 g, 5.99 mmol, 1 eq.) and Boc-Gly-OH (1.57 g, 8.99 mmol, 1.5 eq.) in 100 mL of anhydrous DCM was added EDC (1.72 g, 8.99 mmol, 1.5 eq.) and DMAP (329 mg, 2.69 mmol, 0.45 eq.). The reaction mixture was stirred at 0° C. until HPLC showed complete disappearance of the starting material (approx. 1 hour and 45 minutes). The organic layer was washed with a 0.5% NaHCO$_3$ solution (2×50 mL), water (1×50 mL), a 0.1 N HCl solution (2×50 mL) and brine (1×50 mL); and dried over MgSO$_4$. After filtration and evaporation under vacuum, 4.94 g of crude product were obtained (quantitative yield). The crude solid was used in the next reaction without further purification. $^1$H NMR (300 MHz, CDCl$_3$); δ 0.89 (3H, t, J=7.6 Hz), 0.96 (3H, t, J=7.5 Hz), 1.18 (9H, s), 1.40 (9H, s), 2.07-2.29 (3H, m), 2.64 (2H, q, 7.5 Hz), 4.01-4.22 (2H, m), 5.00 (1H, br s), 5.01 (2H, s), 5.37 (1H, d, J=17.0 Hz), 5.66 (1H, d, J=17.0 Hz), 7.08 (1H, d, J=2.34 Hz), 7.16 (1H, s), 7.37-7.50 (7H, m), 7.77 (4H, d, J=7.6 Hz), 8.05 (1H, d, J=9.4 Hz). $^{13}$C NMR (75.4 MHz, CDCl$_3$): δ 7.52, 13.30, 19.50, 22.86, 26.45, 28.21, 31.64, 42.28, 49.14, 67.00, 76.65, 79.96, 95.31, 110.13, 118.98, 125.75, 126.45, 127.68, 127.81, 130.03, 131.54, 131.92, 135.25, 143.65, 144.91, 145.19, 147.08, 149.27, 154.75, 155.14, 157.10, 166.98, 169.17.

Example 5

TBDPS-(10)-(7-ethyl-10-hydroxycamptothecin)-(20)-Gly.HCl (Compound 7)

To a solution of TBDPS-(10)-(7-ethyl-10-hydroxycamptothecin)-(20)-Gly-Boc (compound 6, 1 g, 1.27 mmol) in 5 mL anhydrous dioxane was added 5 mL of a 4 M solution of HCl in dioxane. The reaction mixture was stirred at room temperature until HPLC showed complete disappearance of the starting material (1 hour). The reaction mixture was added to 50 mL of ethyl ether and the resulting solid was filtered. The solid was dissolved in 50 mL DCM and washed with brine (pH was adjusted to 2.5 by addition of a saturated NaHCO$_3$ solution). The organic layer was dried over MgSO$_4$, filtered and evaporated under vacuum. The residue was dissolved in 5 mL of DCM and precipitated by addition of 50 mL ethyl ether. Filtration afforded 770 mg (84% yield) final product $^1$H NMR (300 MHz, CDCl$_3$): δ 0.84 (3H, t, J=7.6 Hz), 1.05 (3H, J=7.3 Hz), 1.16 (9H, s), 2.15-2.30 (3H, m), 2.59 (2H, q, 7.6 Hz), 4.16 (1H, d, J=17.9 Hz), 4.26 (1H, d, J=17.9 Hz), 5.13 (2H, s), 5.46 (1H, d, J=17.0 Hz), 5.60 (1H, d, J=17.0 Hz), 7.11 (1H, d, J=2.34 Hz), 7.30 (1H, s), 7.40-7.51 (6H, m), 7.56 (1H, dd, J=2.34, 9.4 Hz), 7.77 (4H, dd, J=7.6, 1.6 Hz), 7.98 (1H, d, J=9.1 Hz). $^{13}$C NMR (75.4 MHz, CDCl$_3$): δ 8.09, 13.72, 20.26, 23.61, 26.94, 31.83, 41.01, 50.71, 67.62, 79.51, 97.03, 111.65, 119.69, 127.13, 128.97, 128.99, 129.11, 131.43, 131.96, 133.00, 133.03, 136.51, 145.62, 145.81, 147.24, 148.29, 150.58, 156.27, 158.68, 167.81, 168.34.

Example 6

$^{40k}$4arm-PEG-Gly-(20)-(7-ethyl-10-hydroxycamptothecin)-(10)-TBDPS (Compound 8)

To a solution of $^{40k}$4arm-PEGCOOH (compound 3, 1.4 g, 0.036 mmol, 1 eq.) in 14 mL of anhydrous DCM was added TBDPS-(10)-(7-ethyl-10-hydroxycamptothecin)-(20)-Gly-.HCl (compound 7, 207 mg, 0.29 mmol 2.0 eq. per active site), DMAP (175 mg, 1.44 mmol, 10 eq.) and PPAC (0.85 mL of a 50% solution in EtOAc, 1.44 mmol, 10 eq.). The reaction mixture was stirred at room temperature overnight and then, evaporated under vacuum. The resulting residue was dissolved in DCM and the product was precipitated with ether and filtered. The residue was recrystallized with DMF/IPA to give the product (1.25 g). $^{13}$C NMR (75.4 MHz, CDCl$_3$): δ 7.45, 13.20, 19.39, 22.73, 26.42, 31.67, 40.21, 49.01, 66.83, 95.16, 110.02, 118.83, 125.58, 126.40, 127.53, 127.73, 129.96, 131.49, 131.76, 131.82, 135.12, 143.51, 144.78, 145.13, 146.95, 149.21, 154.61, 156.92, 166.70, 168.46, 170.30.

Example 7

$^{40k}$4arm-PEG-Gly(20)-(7-ethyl-10-hydroxycamptothecin) (Compound 9)

To compound $^{40k}$4arm-PEG-Gly-(20)-(7-ethyl-10-hydroxycamptothecin)-(10)-TBDPS (compound 8, 1.25 g) was added a solution of TBAF (122 mg, 0.46 mmol, 4 eq.) in a 1:1 mixture of THF and a 0.05 M HCl solution (12.5 mL). The reaction mixture was stirred at room temperature for 4 hours and then, extracted with DCM twice. The combined organic phases were dried over MgSO$_4$, filtered and evaporated under vacuum. The residue was dissolved in 7 mL of DMF and precipitated with 37 mL IPA. The solid was filtered and washed with IPA. The precipitation with DMF/IPA was repeated. Finally the residue was dissolved in 2.5 mL of DCM and precipitated by addition of 25 mL of ether. The solid was filtered and dried at 40° C. in vacuum oven overnight (860 mg). $^{13}$C NMR (75.4 MHz, CDCl$_3$): δ 7.48, 13.52, 22.91, 31.67, 40.22, 49.12, 66.95, 94.82, 105.03, 118.68, 122.54, 126.37, 128.20, 131.36, 142.92, 144.20, 144.98, 147.25, 148.29, 156.44, 156.98, 166.82, 168.49, 170.39. This NMR data shows no sign of PEG-COOH which indicates that all of the COOH reacted. The loading, as determined by fluorescence detection was found to be 3.9 which is consistent with full loading of the 7-ethyl-10-hydroxycamptothecin on each of the four branches of the polymer. Repeated runs of this experiments at much larger scale yielded consistent results.

Example 8

Boc-(10)-(7-ethyl-10-hydroxycamptothecin) (Compound 10)

To a suspension of 7-ethyl-10-hydroxycamptothecin (compound 4, 2.45 g, 1 eq.) in 250 mL of anhydrous DCM at room temperature under N$_2$ were added di-tert-butyl dicarbonate (1.764 g, 1.3 eq.) and anhydrous pyridine (15.2 mL, 30 eq.). The suspension was stirred overnight at room temperature. The hazy solution was filtered through celite (10 g) and the filtrate was washed with 0.5 N HCl three times (3×150 mL) and a NaHCO$_3$ saturated solution (1×150 ml). The solution was dried over MgSO$_4$ (1.25 g). The solvent was removed under vacuum at 30° C. The product was dried under vacuum at 40° C. (yield=82%, 2.525 g) $^{13}$C NMR (75.4 MHz, CDCl$_3$) δ 173.53, 157.38, 151.60, 151.28, 150.02, 149.70, 147.00, 146.50, 145.15, 131.83, 127.19, 127.13, 124.98, 118.53, 113.88, 98.06, 84.26, 72.80, 66.18, 49.33, 31.62, 27.73, 23.17, 13.98, 7.90.

Example 9

Boc-(10)-(7-ethyl-10-hydroxycamptothecin)-(20)-Ma-Bsmoc (Compound 11)

To a solution of Boc-(10)-(7-ethyl-10-hydroxycamptothecin) (compound 10, 0.85 g, 1.71 mmol) and Bsmoc-Ala (0.68 g, 2.30 mmol) in anhydrous CH$_2$Cl$_2$ (20 mL) were added EDC (0.51 g, 2.67 mmol) and DMAP (0.065 g, 0.53 mmol) at 0° C. The mixture was stirred at 0° C. for 45 min under N$_2$, then warmed up to room temperature. When completion of the reaction was confirmed by HPLC, the reaction mixture was washed with 1% NaHCO$_3$ (2×50 ml), H$_2$O (50 mL) and 0.1 N HCl (2×50 mL). The organic phase was dried with anhydrous $MgSO_4$ and filtrated. Solvent was removed under reduced pressure. The resulting solid was dried under vacuum below 40° C. overnight to give the product of 1.28 g with the yield of 95%. $^{13}C$ NMR (75.4 MHz, $CDCl_3$) d: 171.16, 166.83, 157.16, 154.78, 151.59, 151.33, 149.82, 147.17, 146.68, 145.35, 145.15, 139.08, 136.88, 133.60, 131.83, 130.45, 130.40, 130.33, 127.40, 127.08, 125.32, 125.14, 121.38, 120.01, 114.17, 95.90, 84.38, 77.19, 76.64, 67.10, 56.66, 53.45, 49.96, 49.34, 31.7, 27.76, 17.94, 14.02, 7.53. ESI-MS, 786.20 $[M+H]^+$.

Example 10

Boc-(10)-(7-ethyl-10-hydroxycamptothecin)-(20)-Ala (Compound 12)

A solution of Boc-(10)-(7-ethyl-10-hydroxycamptothecin)-(20)-Ala-Bsmoc (compound 11, 4.2 g, 5.35 mmol) and 4-piperidinopiperidine (1.17 g, 6.96 mmol) in anhydrous $CH_2Cl_2$ (200 ml) was stirred at room temperature for 5 hours. This mixture was then washed with 0.1 N HCl (2×40 ml), followed by drying the organic layer over anhydrous $MgSO_4$. This solution was filtered, and the solvent was removed by vacuum distillation to yield 2.8 g of product with purity of 93%, determined by HPLC. This product was further purified by trituration with ether (3×20 ml), and then trituration with ethyl acetate (4×20 ml) to yield 1.52 g (2.70 mmol) with purity 97%. $^{13}C$ NMR (75.4 MHz, $CDCl_3$) δ 168.39, 166.63, 156.98, 151.20, 151.15, 149.69, 146.67, 146.56, 145.37, 144.53, 131.66, 127.13, 124.99, 119.80, 113.82, 96.15, 84.21, 77.67, 67.16, 49.48, 49.06, 31.56, 27.74, 23.14, 15.98, 13.98, 7.57.

Example 11

$^{40k}$4arm-PEG-Ala-(20)-(7-ethyl-10-hydroxycamptothecin)-(10)-Boc (Compound 13)

To anhydrous $CH_2Cl_2$ (100 mL) Boc-(10)-(7-ethyl-10-hydroxycamptothecin)-(20)-Ala (compound 12, 1.50 g, 2.5 mmol) and 4armPEG-COOH (compound 3, 10.01 g, 1.0 mmol) were added at room temperature. The solution was cooled to 0° C., followed by addition of EDC (0.29 g, 1.5 mmol) and DMAP (0.30 g, 2.5 mmol). The mixture was stirred at 0° C. for 1 hour under $N_2$. Then it was kept at room temperature overnight. The solvent was evaporated under reduced pressure. The residue was dissolved in 40 mL of DCM, and the crude product was precipitated with ether (300 mL). The wet solid resulting from filtration was dissolved in a mixture of DMF/IPA (60/240 mL) at 65° C. The solution was allowed to cool down to room temperature within 2~3 hours, and the product was precipitated. Then, the solid was filtered and washed with ether (2×200 mL). The wet cake was dried under vacuum below 40° C. overnight to give product of 8.5 g.

Example 12

$^{40k}$4arm-PEG-Ala-(20)-(7-ethyl-10-hydroxycamptothecin) (Compound 14)

To a solution (130 mL) of 30% TFA in anhydrous $CH_2Cl_2$ $^{40k}$4arm-PEG-Ala-(20)-(7-ethyl-10-hydroxycamptothecin)-(10)-Boc (compound 13, 7.98 g) was added at room temperature. The mixture was stirred for 3 hours, or until the disappearance of starting material was confirmed by HPLC. The solvents were removed as much as possible under vacuum at 35° C. The residues were dissolved in 50 mL of DCM, and the crude product was precipitated with ether (350 mL) and filtered. The wet solid was dissolved in a mixture of DMF/IPA (50/200 mL) at 65° C. The solution was allowed to cool down to room temperature within 2~3 hours, and the product was precipitated. Then the solid was filtered and washed with ether (2×200 mL). The wet cake was dried under vacuum below 40° C. overnight to give product of 6.7 g. $^{13}C$ NMR (75.4 MHz, $CDCl_3$) d: 170.75, 169.30, 166.65, 157.00, 156.31, 148.36, 147.19, 145.03, 144.29, 143.00, 131.49, 128.26, 126.42, 122.47, 118.79, 105.10, 94.57, 78.08, 77.81, 77.20, 71.15, 70.88, 70.71, 70.33, 70.28, 70.06, 69.93, 69.57, 66.90, 49.14, 47.14, 31.53, 22.95, 17.78, 13.52, 7.46.

Example 13

Boc-(10)-(7-ethyl-10-hydroxycamptothecin)-(20)-Met-Bsmoc (Compound 15)

To a solution of Boc-(10)-7-ethyl-10-hydroxycamptothecin (compound 10, 2.73 g, 5.53 mmol) and Bsmoc-Met (3.19 g, 8.59 mmol) in anhydrous $CH_2Cl_2$ (50 mL) were added EDC (1.64 g, 8.59 mmol) and DMAP (0.21 g, 1.72 mmol) at 0° C. The mixture was stirred at 0° C. for 45 minutes under $N_2$, then warmed up to room temperature. When completion of the reaction was confirmed by HPLC, the reaction mixture was washed with 11% $NaHCO_3$ (2×100 ml), $H_2O$ (100 mL) and 0.1 N HCl (2×100 mL). The organic phase was dried with anhydrous $MgSO_4$ and filtrated. Solvents were removed under reduced pressure. The resulting solid was dried under vacuum below 40° C. overnight to give the product of 4.2 g with the yield of 88%. $^{13}C$ NMR (75.4 MHz, $CDCl_3$) d: 170.3, 166.8, 157.1, 155.2, 151.4, 151.2, 149.7, 147.0, 146.6, 145.3, 145.1, 138.9, 136.6, 133.5, 131.7, 130.5, 130.3, 130.2, 127.3, 127.0, 125.3, 125.1, 121.2, 119.8, 114.1, 96.1, 84.3, 76.7, 67.0, 56.7, 53.5, 53.4, 49.3, 31.6, 31.0, 29.7, 27.7, 23.1, 15.4, 13.9, 7.4; ESI-MS, 846.24 $[M+H]^+$.

Example 14

Boc-(10)-(7-ethyl-10-hydroxycamptothecin)-(20)-Met-$NH_2$.HCl (Compound 16)

A solution of Boc-(10)-(7-ethyl-10-hydroxycamptothecin)-(20)-Met-Bsmoc (compound 15, 4.1 g, 4.85 mmol.) and 4-piperidinopiperidine (1.06 g, 6.31 mmol) in anhydrous $CH_2Cl_2$ (200 mL) was stirred at room temperature for 5 hours. This mixture was then washed with 0.1 N HCl (2×40 ml), followed by drying the organic layer over anhydrous $MgSO_4$. This solution was filtered, and the solvent was removed by vacuum distillation to yield 2.8 g of product with purity of about 97%, determined by HPLC. This product was further purified by trituration with ether (3×20 ml), and then trituration with ethyl acetate (4×20 ml) to yield 1.54 g with purity of 97%. $^{13}C$ NMR (75.4 MHz, $CDCl_3$) d: 167.2, 166.5, 156.9, 151.12, 150.9, 149.8, 146.3, 145.9, 145.8, 144.9, 131.3, 127.2, 127.0, 125.1, 119.6, 113.8, 96.7, 84.3, 78.2, 67.0, 60.4, 52.2, 49.4, 31.4, 29.6, 29.1, 27.7, 23.2, 15.1, 13.9, 7.7.

Example 15

$^{40k}$4arm-PEG-Met-(20)-(7-ethyl-10-hydroxycamptothecin)-(10)-Boc (Compound 17)

To an anhydrous $CH_2Cl_2$ (80 mL) solution, Boc-(10)-(7-ethyl-10-hydroxycamptothecin)-(20)-Met (compound 16, 1.48 g, 2.25 mmol) and 4arm-PEG-COOH (compound 3, 9.0 g, 0.9 mmol) were added at room temperature. The solution was cooled to 0° C., followed by addition of EDC (0.26 g, 1.35 mmol) and DMAP (0.27 g, 2.25 mmol). The mixture was stirred at 0° C. for 1 hour under $N_2$. Then it was kept at room temperature overnight. The reaction mixture was diluted with 70 ml of $CH_2Cl_2$, extracted with 30 ml of 0.1 N HCl/1M NaCl aqueous solution. After the organic layer was dried with $MgSO_4$, the solvent was evaporated under reduced pressure. The residue was dissolved in 40 mL of $CH_2Cl_2$, and the crude product was precipitated with ether (300 mL). The wet solid resulting from filtration was dissolved in 270 mL of DMF/IPA at 65° C. The solution was allowed to cool down to room temperature within 2~3 hours, and the product was precipitated. Then the solid was filtered and washed with ether (2×400 mL). The above crystallization procedure in DMF/IPA was repeated. The wet cake was dried under vacuum below 40° C. overnight to give product of 7.0 g. $^{13}C$ NMR (75.4 MHz, $CDCl_3$) d: 169.8, 169.6, 166.5, 156.9, 151.2, 151.1, 149.9, 147.0, 146.6, 145.0, 131.7, 127.1, 126.8, 124.9, 119.7, 113.8, 95.5, 84.1, 70.1, 69.9, 66.9, 50.7, 49.2, 31.5, 31.2, 29.6, 27.6, 23.1, 15.3, 13.9, 7.5.

Example 16

$^{40k}$4arm-PEG-Met-(20)-(7-ethyl-10-hydroxycamptothecin) (Compound 18)

To a solution of 30% TFA in anhydrous $CH_2Cl_2$ (100 mL), dimethyl sulfide (2.5 mL) and 4arm-PEG-Met-(20)-(7-ethyl-10-hydroxycamptothecin)-(10)-Boc (compound 17, 6.0 g) were added at room temperature. The mixture was stirred for 3 hours, or until disappearance of starting material was confirmed by HPLC. Solvents were removed as much as possible under vacuum at 35° C. The residues were dissolved in 50 mL of $CH_2Cl_2$, and the crude product was precipitated with ether (350 ml), and filtered. The wet solid was dissolved in a mixture of DMF/IPA (60/300 mL) at 65° C. The solution was allowed to cool down to room temperature within 2~3 hours, and the product was precipitated. Then the solid was filtered and washed with ether (2×200 mL). The wet cake was dried under vacuum below 40° C. overnight to give product of 5.1 g. $^{13}C$ NMR (75.4 MHz, $CDCl_3$) d: 169.7, 166.6, 157.0, 156.3, 148.4, 147.3, 145.0, 144.4, 142.9, 131.5, 128.3, 126.4, 122.5, 118.7, 105.2, 94.7, 78.1, 67.0, 50.7, 49.2, 31.6, 31.3, 29.7, 23.0, 15.3, 13.5, 7.5; Ratio of 7-ethyl-10-hydroxycamptothecin to PEG: 2.1% (wt).

Example 17

Boc-(10)-(7-ethyl-10-hydroxycamptothecin)-(20)-Sar-Boc (Compound 19)

Boc-Sar-OH (432 mg, 2.287 mmol) was added to a solution of Boc-(10)-(7-ethyl-10-hydroxycamptothecin) (compound 10, 750 mg, 1.52 mmol) in 75 mL of DCM and cooled to 0° C. DMAP (432 mg, 2.287 mmol) and EDC (837 mg, 0.686 mmol) were added and the reaction mixture was stirred from 0° C.—room temperature for 1.5 hours. Reaction mixture was then washed with 0.5% $NaHCO_3$ (75 mL×2), with water (75 ml×2) and finally washed with 0.1 N HCl (75 mL×1). The methylene chloride layer was dried over $MgSO_4$ and the solvent was evaporated under vacuum and dried. Yield=0.900 mg. (89%). The structure was confirmed by NMR.

Example 18

7-ethyl-10-hydroxycamptothecin-(20)-Sar.TFA (Compound 20)

Boc-(10)-(7-ethyl-10-hydroxycamptothecin)-(20)-Sar-Boc (compound 19, 900 mg, 1.357 mmol) was added to a solution of 4 mL TFA and 16 mL DCM, and stirred at room temperature for 1 hour. The reaction mixture was evaporated with toluene at 30° C. The residue was dissolved in 10 mL $CHCl_3$ and precipitated with ethyl ether. The product was filtered and dried. Yield 700 mg (1.055 mmol, 78%). $^{13}C$ NMR (67.8 MHz, $CDCl_3$) δ 168.26, 167.07, 158.84, 158.71, 148.82, 147.94, 147.22, 146.34, 144.04, 131.18, 130.08, 128.97, 124.46, 119.78, 106.02, 97.23, 79.84, 79.34, 66.87, 50.84, 49.86, 31.81, 23.94, 15.47, 13.84, 8.08.

Example 19

TBDMS-(10)-(7-ethyl-10-hydroxycamptothecin)-(20)-Sar.HCl (Compound 21)

A solution of the 7-ethyl-10-hydroxycamptothecin-(20)-Sar.TFA (compound 20, 2.17 g, 3.75 mmol, 1 eq.) in anhydrous DMF (30 mL) was diluted with 200 mL of anhydrous DCM. $Et_3N$ (2.4 mL, 17.40 mmol, 4.5 eq.) was added followed by TBDMSCl (2.04 g, 13.53 mmol, 3.5 eq.). The reaction mixture was stirred at room temperature until HPLC showed disappearance of the starting material (approximately 1 hour). The organic layer was washed with 0.5% $NaHCO_3$ twice, water once, and a 0.1 N HCl solution saturated with brine twice; and then dried over $MgSO_4$. After filtration and evaporation of the solvent under vacuum, the resulting oil was dissolved in DCM. Addition of ether gave a solid that was filtered using a fine or medium buchner funnel (2.00 g, 87% yield). HPLC of the solid showed 96% purity.

$^1H$ NMR and $^{13}C$ NMR confirmed the structure. $^1H$ NMR (300 MHz, $CD_3OD$): δ 0.23 (6H, s), 0.96 (9H, s), 0.98 (3H, t, J=7.3 Hz), 1.30 (3H, t, J=7.6 Hz), 2.13-2.18 (2H, m), 2.67 (3H, s), 3.11 (3H, q, J=7.6 Hz), 4.10 (1H, d, J=17.6 Hz), 4.22 (1H, d, J=17.6 Hz), 5.23 (2 H, s), 5.40 (1H, d, J=16.7 Hz), 5.55 (1H, d, J=16.7 Hz), 7.32 (1H, s), 7.38-7.43 (2H, m), 8.00 (1H, d, J=9.1 Hz). $^{13}C$ NMR (75.4 MHz, $CD_3OD$): δ −4.14, 8.01, 14.10, 19.30, 23.98, 26.16, 31.78, 33.52, 49.46, 50.95, 67.66, 79.80, 97.41, 111.96, 119.99, 127.75, 129.28, 129.67, 131.57, 145.24, 146.86, 147.16, 148.02, 150.34, 156.69, 158.72, 167.02, 168.27.

Example 20

$^{40k}$4arm-PEG-Sar-(20)-(7-ethyl-10-hydroxycamptothecin)-(10)-TBDMS (Compound 22)

To a solution of $^{40K}$4arm-PEG-COOH (compound 3, 10 g, 0.25 mmol, 1 eq.) in 150 mL of anhydrous DCM was added a solution of TBDMS-(10)-(7-ethyl-10-hydroxycamptothecin)-Sar.HCl (compound 21, 1.53 g, 2.5 mmol, 2.5 eq.) in 20 mL of anhydrous DMF and the mixture was cooled to 0° C. To this solution were added EDC (767 mg, 4 mmol, 4 eq.) and DMAP (367 mg, 3 mmol, 3 eq.) and the reaction mixture was allowed to warm to room temperature slowly and stirred at room temperature overnight. Then, the reaction mixture was evaporated under vacuum and the residue was dissolved in a minimum amount of DCM. After addition of ether, solid was formed and filtered under vacuum. The residue was dissolved in 30 mL of anhydrous CH₃CN and precipitated by addition of 600 mL IPA. The solid was filtered and washed with IPA and ether to give the product (9.5 g). The structure was confirmed by NMR.

Example 21

$^{40K}$4arm-PEG-Sar-(20)-(7-ethyl-10-hydroxycamptothecin) (Compound 23)

Method A. $^{40K}$4arm-PEG-Sar-(20)-(7-ethyl-10-hydroxycamptothecin)-(10) TBDMS (compound 22) was dissolved in a 50% mixture of TFA in H₂O (200 mL). The reaction mixture was stirred at room temperature for 10 hours and then, diluted with 100 mL of H₂O and extracted with DCM (2×300 mL). The combined organic phases were washed with H₂O (2×100 mL), dried over MgSO₄, filtered and evaporated under vacuum. The residue was dissolved in 100 mL of anhydrous DMF gently heated with a heat gun and precipitated by slow addition of 400 mL DMF. The solid was filtered and washed with 20% DMF in IPA and ether. The solid was dissolved in DCM and precipitated with ether (6.8 g). The structure was conformed by NMR.

Method B. $^{40K}$4arm-PEG-Sar-(20)-(7-ethyl-10-hydroxycamptothecin)-(10)-TBDMS (1 g) was dissolved in 10 mL of a 1N HCl solution. The reaction mixture was stirred at room temperature for 1 hour (checked by HPLC) and then extracted with DCM (2×40 mL). The organic layers were dried over MgSO₄, filtered and evaporated under vacuum. The resulting bright yellow residue was dissolved in 10 mL of DMF (slightly heated with a heat gun) and then 40 mL of IPA were added. The resulting solid was filtered and dried overnight at 40° C. in a vacuum oven. The structure was confirmed by NMR.

Biological Data

Example 22

Toxicity Data

A maximum tolerated dose (MTD) of four-arm PEG conjugated 7-ethyl-10-hydroxycamptothecin was studied using nude mice. Mice were monitored for 14 days for mortality and signs of illness and sacrificed when body weight loss was >20% of the pretreatment body weight.

Table 1 shows the maximum tolerated dose of each compound for both single dose and multiple dose administration. Each dose for multiple dose administration was given mice every other day for 10 days and the mice were observed for another 4 days, thus for total 14 days.

TABLE 1

MTD Data in Nude Mice

| Compound | Dose Level (mg/kg) | Survival/Total | Comments |
|---|---|---|---|
| Compound 9 | 25 | 5/5 | |
| Single dose | 30 | 5/5 | |
|  | 35 | 4/5 | Mouse euthanized due to >20% body weight loss |

TABLE 1-continued

MTD Data in Nude Mice

| Compound | Dose Level (mg/kg) | Survival/Total | Comments |
|---|---|---|---|
| Compound 9 | 10 | 5/5 | |
| Multiple dose* | 15 | 3/5 | Mice euthanized due to >20% body weight loss |
|  | 20 | 0/5 | Mice euthanized due to >20% body weight loss |

The MTD found for 4arm-PEG-Gly-(7-ethyl-10-hydroxycamptothecin) (compound 9) was 30 mg/kg when given as single dose, and 10 mg/kg when given as multiple dose (q2d× 5).

Example 23

In Vitro Data

In Table 2, the cytotoxicity (µM of each compound that results in an $IC_{50}$) provides an indication of the in vitro anti-tumor potency of each compound. This study was used to determine the effect of PEGylation of four-arm PEGylated 7-ethyl-10-hydroxycamptothecin conjugates. The in vitro cytotoxicity of PEG-Gly-(7-ethyl-10-hydroxycamptothecin), 7-ethyl-10-hydroxycamptothecin, and CPT-1 was determined using a MTS assay. Cells were incubated with drugs for 72 hours at 37° C. Following incubation, MTS dye was added and formation of a colored product (formazan) was measured at 490 nm.

The $IC_{50}$ values of four-arm PEG-Gly-(7-ethyl-10-hydroxycamptothecin) and CPT-11 indicate that four-arm PEG-Gly-(7-ethyl-10-hydroxycamptothecin) have much higher in vitro inhibition in all tested tumor cells than CPT-11. In addition, four-arm PEG-Gly-(7-ethyl-10-hydroxycamptothecin) has significantly higher in vitro inhibition of the tested tumor cells except for HT29 tumor cells than native 7-ethyl-10-hydroxycamptothecin.

PEG-Gly-(7-ethyl-10-hydroxycamptothecin) conjugates were about 10, to 600 fold more potent than Camptosar ®. PEG-Gly-(7-ethyl-10-hydroxycamptothecin) conjugates were 8 to 16 fold more sensitive than Pegamotecan (a PEGylated prodrug of camptothecin) in COLO 205, HT-29 and OVCAR-3 cell lines.

TABLE 2

$IC_{50}$ (µM) data

| Cancer Type | Cell Line | 7-ethyl-10-hydroxycamptothecin | Compound 9 | CPT-11 |
|---|---|---|---|---|
| Colorectal | Colo 205 | 0.2 ± 0.2 | 1.0 ± 0.6 | 11 ± 1.4 |
|  | HT29 | 0.1 ± 0.04 | 0.5 ± 0.3 | 27 ± 8.6 |
| Lung | A549 | 1.0 ± 0.1 | 2.7 ± 0.4 | 67 ± 17 |
| Pancreatic | PANC-1 | 0.56 ± 0.38 | 0.67 ± 0.14 | 34 ± 16 |
|  | MIA PaCa-2 | 0.18 | 0.09 | 67 ± 46 |
|  | ASPC-1 | 0.64 ± 0.13 | 1.6 ± 1.1 | 33 ± 1.0 |
|  | BxPC-3 | 0.54 ± 0.58 | 0.24 ± 0.04 | 44 ± 44 |
| Ovarian | OVCAR-3 | 0.1 ± 0.02 | 0.3 ± 0.2 | 20 ± 7.1 |
|  | OV90 | 0.1 ± 0.02 | 0.6 ± 0.7 | 18 ± 4.8 |
|  | OVCAR-8 | 0.03 ± 0.01 | 0.5 ± 0.1 | 9.0 ± 1.3 |
|  | A2780 | 0.02 ± 0.01 | 0.2 ± 0.2 | 8.0 ± 3.5 |
|  | SK-OV-3 | 0.2 ± 0.1 | 0.9 ± 0.01 | 52 ± 8.5 |

$IC_{50}$ of 4armPEG-Gly-(7-ethyl-10-hydroxycamptothecin) (compound 9) is expressed in terms of 7-ethyl-10-hydroxycamptothecin equivalents.
Values shown are average ± SD (n = 3); where no SD is shown, the value shown is an average of two replicates.

PEG-Gly-(7-ethyl-10-hydroxycamptothecin) conjugates containing various amino acids are potent in vitro cytotoxicity against a panel of cancer cell lines as summarized in TABLE 3. All the PEG-7-ethyl-10-hydroxycamptothecin conjugates showed potent in vitro anti-tumor activities which exceed the activity of small molecule prodrug CPT-11 and Pegamotecan.

TABLE 3

$IC_{50}$ (µM) data of
Various PEG-(7-ethyl-10-hydroxycamptothecin) Conjugates

| Compound | Colorectal | | Ovarian | Lung |
|---|---|---|---|---|
| | Colo 205 | HT29 | OVCAR-3 | A549 |
| Compound 12 (Ala) | 0.03 | 0.16 | 0.14 | 4.4 |
| Compound 23 (Sar) | 0.04 | 0.27 | 0.17 | 11 |
| Compound 18 (Met) | 0.03 | 0.14 | 0.13 | 1.6 |

TABLE 3-continued $IC_{50}$ (µM) data of
Various PEG-(7-ethyl-10-hydroxycamptothecin) Conjugates

| Compound | Colorectal | | Ovarian | Lung |
|---|---|---|---|---|
| | Colo 205 | HT29 | OVCAR-3 | A549 |
| 7-ethyl-10-hydroxy-camptothecin | 0.08 | 0.08 | ND | ND |
| CPT-11 | 20 | 56 | 41 | 13 |

Example 24

In Vivo Data-Single Dose Efficacy in Breast Tumor Xenograft Mice

The efficacy of four-arm PEG-Gly-(7-ethyl-10-hydroxycamptothecin) conjugates (compound 9) against a subcutaneous human mammary carcinoma (MX-1) grown in nude mice was determined as follows. Following at least one week of acclimation, tumors were established by implanting small tumor fragments from donor mice into a single subcutaneous site, on the left auxiliary flank region of nude mice. The tumor implantation site was observed twice weekly and measured once palpable. The tumor volume for each mouse was determined by measuring two dimensions with calipers and calculated using the formula: tumor volume=(length×width$^2$). When tumors reached the average volume of approximately 100 mm$^3$, the mice were divided into their experimental groups, which consists of untreated controls, four-arm PEG-Gly-(7-ethyl-10-hydroxycamptothecin) made as per Example 7 herein, PEG-Ala-CPT prepared as described in Conover et al. (*Anti-Cancer Drug Design*, 1999, 14:499-506), the contents of which are incorporated by reference herein and CPT-11. Drugs were administered intravenously via the tail vein as a single dose of 20 mg/kg body weight of a mouse. The dose of the conjugate refers to the amount equivalent to 7-ethyl-10-hydroxycamptothecin. Mouse weight and tumor sizes were measured at the beginning of study and on the 31$^{st}$ day after the single dose administration.

Table 4 shows tumor shrinkages measured in mice xenografted with MX-1 breast tumor cells on the 31$^{st}$ day after a single dose i.v. injection of 20 mg/kg body weight of a mouse. The overall growth of tumors was calculated as the mean tumor volume (TV). A percent treatment over control (T/C) was also calculated. The percentage of tumor regression indicates the in vivo activity of each compound. Four-arm PEG-GLY-7-ethyl-10-hydroxycamptothecin conjugates showed significant anti-tumor activity with 100% survival of the mice and 100% cure. Both CPT-11 and saline control showed no protection with 0% survival. All the data are summarized in Table 4.

TABLE 4

Single Dose Efficacy Comparison in MX-1 Breast Tumor Xenograft Mouse Model

| Compound | Mean TV ± SD (mm$^3$) | Median TV (mm$^3$) | F/I (%) | Chg in TV ± SD (%) | TGI (%) | Regressions (%) | Cures (%) | Survival (%) | T/C (%) |
|---|---|---|---|---|---|---|---|---|---|
| Control | 1136 ± 686 | 785 | 1259 | 1399 ± 658 | 0 | 0 | 0 | 0 | — |
| Compound 9 | 7 ± 9 | 3 | 7 | −94 ± 10 | 99 | 100 | 100 | 100 | 0.3 |
| PEG-Ala-CPT | 43 ± 41 | 40 | 42 | −40 ± 93 | 96 | 50 | 33 | 100 | 5 |
| CPT-11 | 845 ± 50 | 845 | 843 | 1424 ± 432 | 26 | 0 | 0 | 0 | 108 |

The results show that the four-arm PEG-Gly-(7-ethyl-10-hydroxycamptothecin) is significantly more effective than either PEG-Ala-CPT or CPT-11 in the treatment of breast cancer.

In breast MX-1 tumor model, treatment with 4armPEG-Gly-(7-ethyl-10-hydroxycamptothecin) led to almost 100% tumor growth inhibition and complete cures of all the animals. At equivalent dose levels, treatment with CPT-11 caused a 26% tumor growth inhibition.

Example 25

In Vivo Data-Multiple Dose Efficacy in Breast Tumor Xenograft Mice

The efficacy of a series of four-arm PEG-Amino acid (derivative)-(7-ethyl-10-hydroxycamptothecin) conjugates against a human mammary carcinoma (MX-1) grown in nude mice was determined. The mice were assigned to groups each receiving 4arm-PEG-Ala-(7-ethyl-10-hydroxycamptothecin), 4arm-PEG-Gly-(7-ethyl-10-hydroxycamptothecin), 4arm-PEG-Met-(7-ethyl-10-hydroxycamptothecin), 4arm-PEG-Sar-(7-ethyl-10-hydroxycamptothecin), each made as described herein, CPT-11 or saline control. The mice were dosed 5 mg/kg/day for six consecutive days (every 2 days [q×2d]×6). Mouse weight and tumor sizes were monitored up to the 31$^{st}$ day after the first dose administration and subsequent administrations.

Table 5 shows tumor shrinkages measured in mice xenografted with MX-1 breast tumor cells on the 31$^{st}$ day after the i-v. injection of 5 mg/kg/dose for six days (q2d×6). All four-arm PEG-Amino acid (derivative)-(7-ethyl-10-hydroxycamptothecin) conjugates showed significant anti-tumor activity with 100% survival of the mice and 100% regression. Both CPT-11 and saline control showed no protection with 0% survival. All the data are summarized in Table 5.

In Mx-1 breast tumor model with a single dose or multiple dose injections, 4armPEG-Gly-(7-ethyl-10-hydroxycamptothecin) effectively suppressed tumor growth in both small (100 mm$^3$) and large (450 mm$^3$) bulky established tumors.

TABLE 5

Multiple Dose Efficacy Comparison in MX-1 Breast Tumor Xenograft Mouse Model

| Compound | Mean TV ± SD (mm$^3$) | Median TV (mm$^3$) | F/I (%) | Chg in TV ± SD (%) | TGI (%) | Regressions (%) | Cures (%) | Survival (%) | T/C (%) |
|---|---|---|---|---|---|---|---|---|---|
| Control | 1136 ± 686 | 785 | 1259 | 1399 ± 658 | 0 | 0 | 0 | 0 | — |
| Compound 12 (Ala) | 10 ± 11 | 9.6 | 10 | −91 ± 11 | 99 | 100 | 67 | 100 | 1.2 |
| Compound 9 (Gly) | 12 ± 18 | 6.6 | 14 | −91 ± 10 | 99 | 100 | 100 | 100 | 0.8 |
| Compound 18 (Met) | 8 ± 9 | 5.6 | 7.8 | −94 ± 7 | 99 | 100 | 100 | 100 | 0.7 |
| Compound 23 (Sar) | 12 ± 10 | 14.6 | 13 | −87 ± 12 | 99 | 100 | 100 | 100 | 1.9 |
| CPT-11 | 632 ± 698 | 340 | 594 | 423 ± 243 | 44 | 0 | 0 | 0 | 43 |

The data shows that the four-arm PEG-Amino acid derivatives of 7-ethyl-10-hydroxycamptothecin are significantly more effective than CPT-11 in the treatment of breast cancer.

Example 26

In Vivo Efficacies in Small and Large Breast Tumor Xenografted Mice

The antitumor efficacy of 4armPEG-Gly-(7-ethyl-10-hydroxycamptothecin) was evaluated in nude mice bearing small (about 100 mm$^3$) or large (about 450 mm$^3$) established human mammary, MX-1 tumors. The antitumor therapeutic activities were determined in mice both with a single dose or multiple dose regimens. In mice xenografted with small breast tumors, treatment with a single of 4armPEG-Gly-(7-ethyl-10-hydroxycamptothecin) (20 mg/kg) led to 100% TGI. Treatment with multiple doses of 4armPEG-Gly-(7-ethyl-10-hydroxycamptothecin) (20 mg/kg q2d×5) also led to 100% TGI. Single dose (20 mg/kg) administration of CPT-11 did not inhibit tumor growth and multiple doses of CPT-11 (20 mg/kg q2d×5) resulted in 44% TGI as of day 31.

Figure 6:
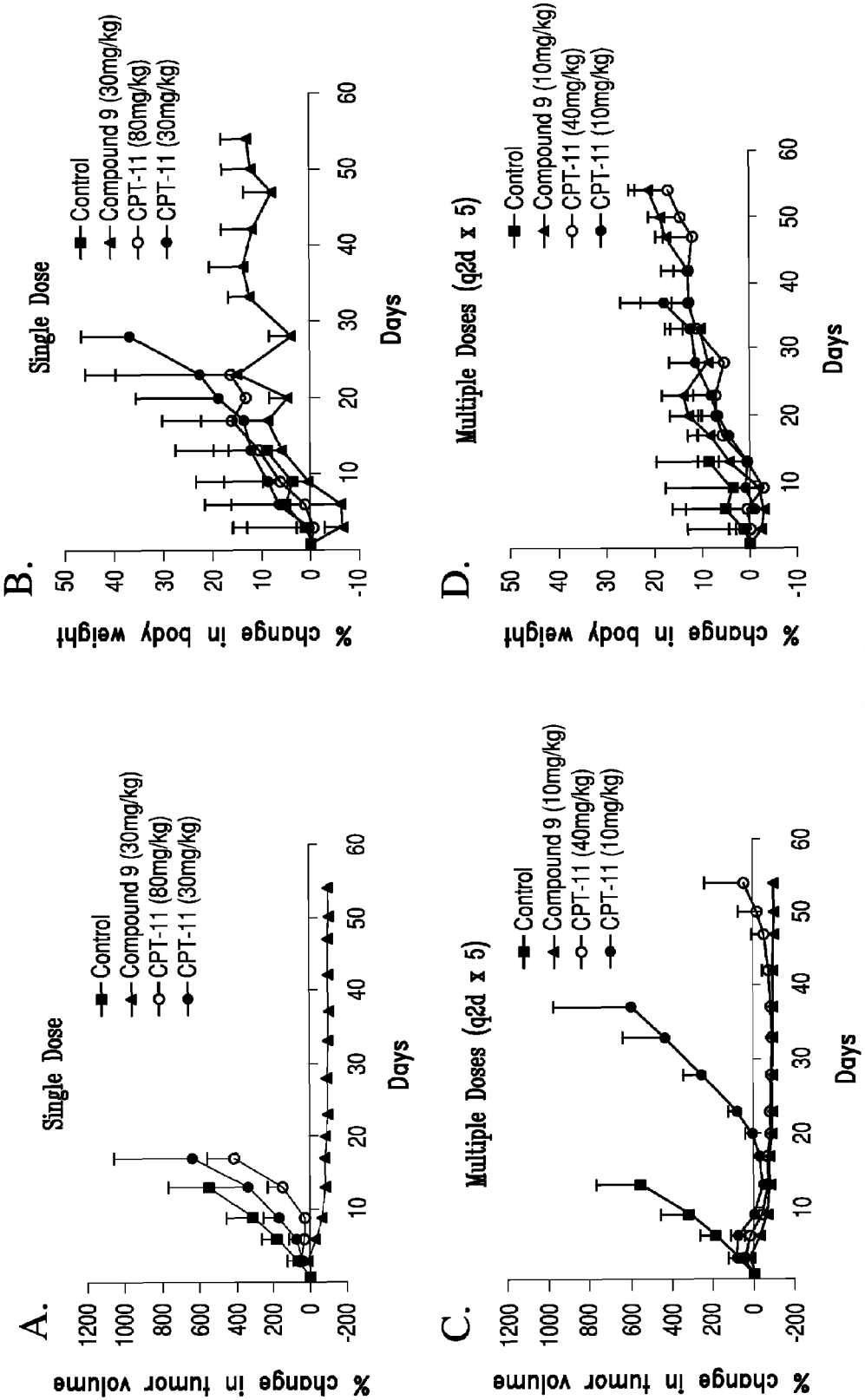
FIG. 6 shows single dose and multiple dose efficacies in large MX-1 breast tumor xenografted mice described in Example 26.

In mice bearing large breast tumors; treatment with a single MTD of 4armPEG-Gly-(7-ethyl-10-hydroxycamptothecin) (30 mg/kg) led to 96% TGI. Four of six mice were cured as of day 54. Treatment with a single MTD of CPT-11 (80 mg/kg) resulted in 70% TGI on day 13. All animals were sacrificed by day 20 due to excessive tumor burden. Treatment with multiple doses of 4armPEG-Gly-(7-ethyl-10-hydroxycamptothecin) at its MTD (10 mg/kg q2d×5) also led to 96% TGI, and five of six mice were cured as of day 54. CPT-11, when given as multiple doses at its MTD (40 mg/kg q2d×5), led to 95% TGI as of day 13. However, tumors regrew in four of the six mice after ~5 weeks. CPT-11, when given at equivalent dose levels as 4armPEG-Gly-(7-ethyl-10-hydroxycamptothecin) (10 mg/kg q2d×5), had effective TGI until treatment was discontinued, after which tumors regrew. The results are set forth in FIGS. 6A and 6C. The antitumor effects are not attributed to a general toxic effect, since treatment with either 4armPEG-Gly-(7-ethyl-10-hydroxy-camptothecin) or CPT-11, when given at the MTD, did not significantly decrease the body weight of the animals for the duration of the treatment as shown in FIGS. 6B and 6D.

Tumors in size of from about 75 mm$^3$ to about 450 mm$^3$ were successfully treated in MX-1 breast tumor xenografted mice.

Example 27

In Vivo Data-Single Dose Efficacy in Colorectal Tumor Xenograft Mice

Figure 7:
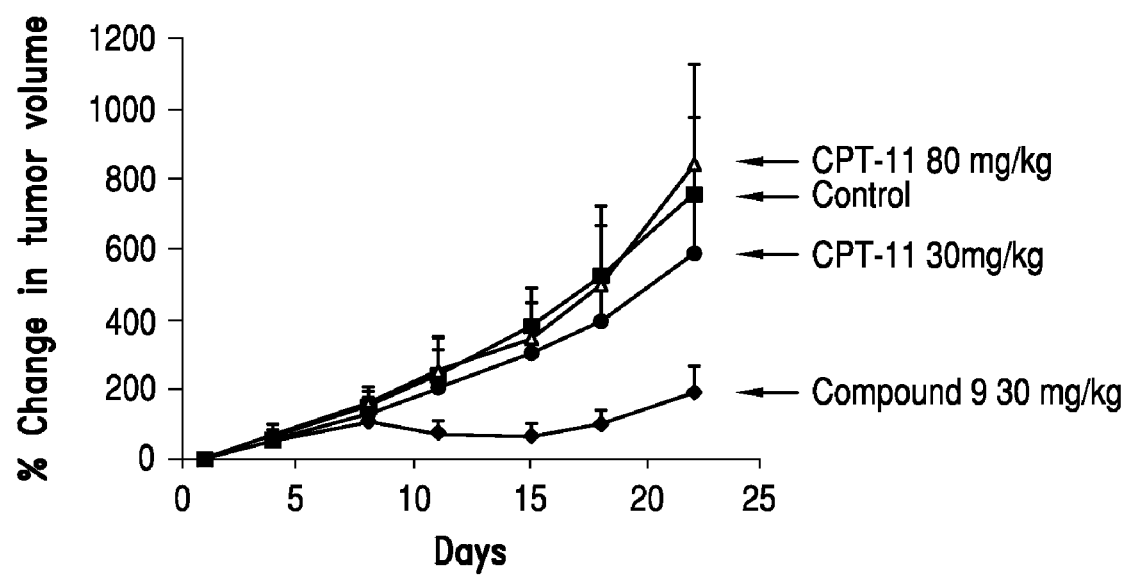
FIG. 7 shows single dose efficacies in HT-29 colorectal tumor xenografted mice described in Example 27.

In this example, tumor shrinkage was measured in mice xenografted with HT-29 colorectal tumor cells on the day 4, 8, 11, 15, 18, and 22 after a single dose intravenous injection of 30 mg/kg of four-arm PEG-Gly-(7-ethyl-10-hydroxycamptothecin) or CPT-11. CPT 11 was also dosed 80 mg/kg. The results are set forth in FIG. 7. Four-arm PEG-Gly-(7-ethyl-10-hydroxycamptothecin) conjugates showed significant anti-tumor activity. Saline control showed no protection with 0% survival. The results show that the four-arm PEG-Gly-(7-ethyl-10-hydroxycamptothecin) is significantly effective than CPT-11 in the treatment of colorectal cancer.

Example 28

In Vivo Data-Multiple Dose Efficacy in Colorectal Tumor Xenograft Mice

Figure 8:
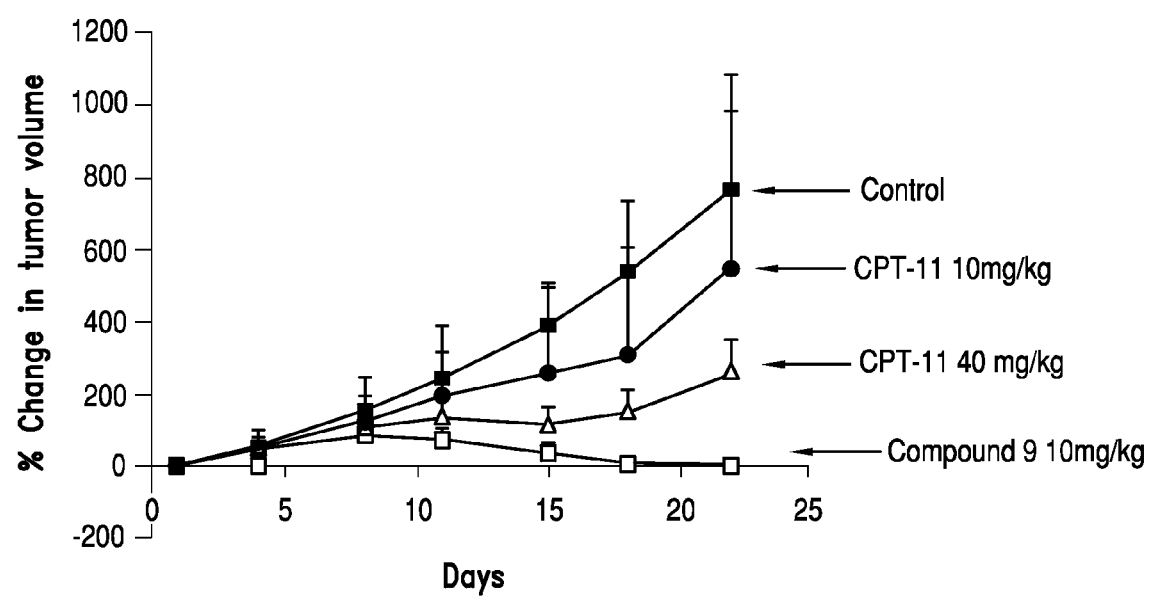
FIG. 8 shows multiple dose efficacies in HT-29 colorectal tumor xenografted mice described in Example 28.

The tumor shrinkage was measured in mice xenografted with HT-29 colorectal tumor cells on the day 4, 8, 11, 15, 18, and 22 after an intravenous injection of 10 mg/kg/dose of four-arm PEG-Gly-(7-ethyl-10-hydroxycamptothecin) or CPT-11 for five days. CPT-11 was also given 40 mg/kg/dose for five days. The results are set forth in FIG. 8. Similar results were obtained with multiple dose administration. Furthermore, multiple dose administration of four-arm PEG-Gly-(7-ethyl-10-hydroxycamptothecin) shows significant therapeutic efficacy compared to that of CPT-11. The results show that multiple doses of four-arm PEG-Gly-(7-ethyl-10-hydroxycamptothecin) is significantly more effective than CPT-11 in the treatment of colorectal cancer. As observed in the MX-1 tumor xenografted mice, treatment with 4armPEG-Gly-(7-ethyl-10-hydroxycamptothecin) or CPT-11 did not significantly decrease the body of weight of the mice during the treatment.

Example 29

In Vivo Data-Single Dose Efficacy in Pancreatic Tumor Xenograft Mice

Figure 9:
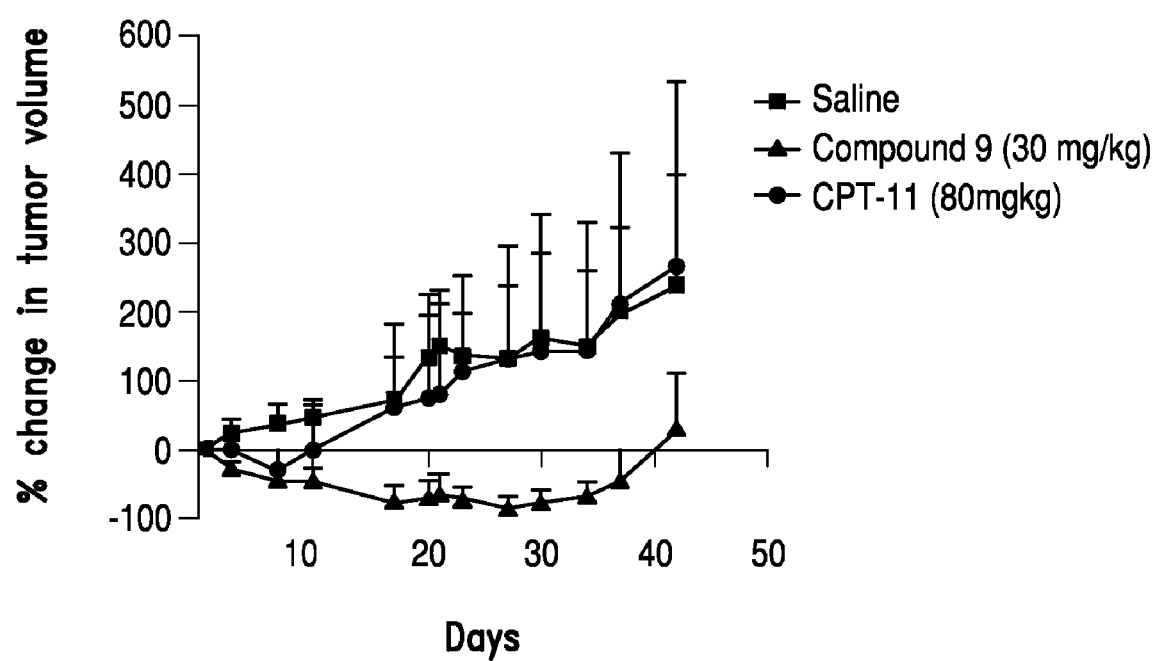
FIG. 9 shows single dose efficacies in MiaPaCa-2 pancreatic tumor xenografted mice described in Example 29.

In this example, tumor shrinkage was measured in mice xenografted with MiaPaCa-2 pancreatic tumor cells on the day 4, 8, 11, 15, 18, and 22 after a single dose intravenous injection of 30 mg/kg of four-arm PEG-Gly-(7-ethyl-10-hydroxycamptothecin) or CPT-11. CPT 11 was also dosed 80 mg/kg. The results are set forth in FIG. 9. Four-arm PEG-Gly-(7-ethyl-10-hydroxycamptothecin) conjugates showed significant antitumor activity. Saline control and CPT-11 showed no protection. The results show that the four-arm PEG-Gly-(7-ethyl-10-hydroxycamptothecin) is significantly effective than CPT-11 in the treatment of pancreatic cancer. Treatment with a single does of 4armPEG-Gly-(7-ethyl-10-hydroxycamptothecin) resulted in 71% TGI, whereas CPT-11 therapy as a single dose injection caused 0% TGI.

Example 30

In Vivo Data-Multiple Dose Efficacy in Pancreatic Tumor Xenograft Mice

Figure 10:
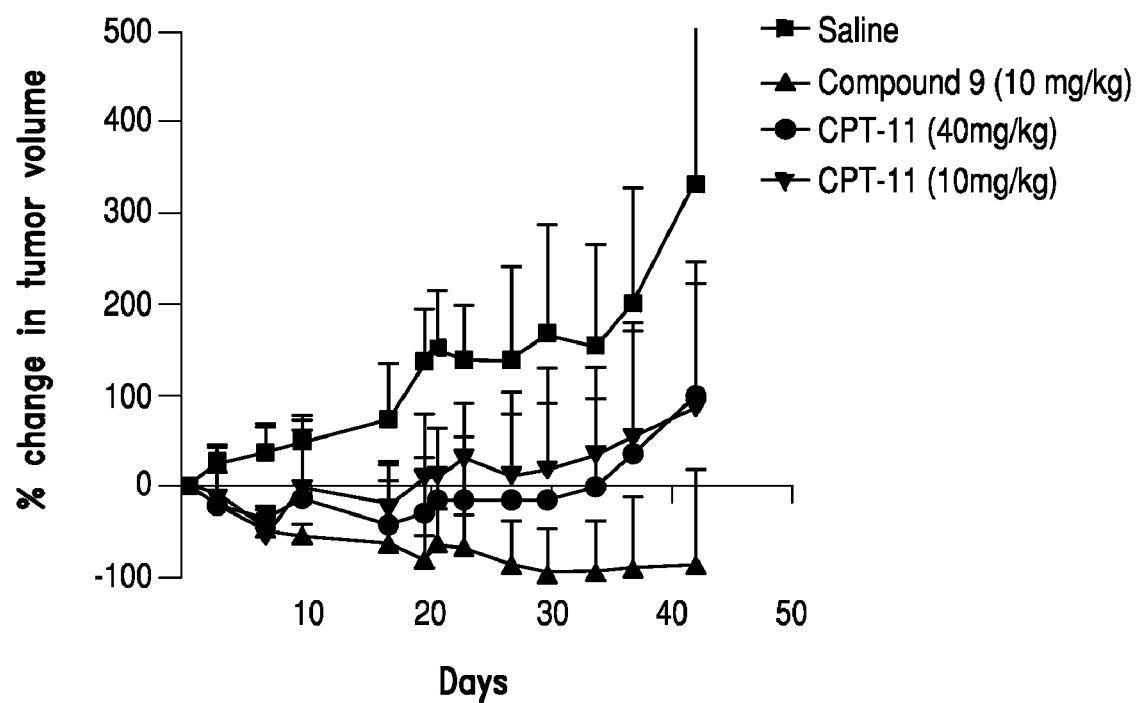
FIG. 10 shows multiple dose efficacies in MiaPaCa-2 pancreatic tumor xenografted mice described in Example 30.

The tumor shrinkage was measured in mice xenografted with MiaPaCA-2 pancreatic tumor cells on the day 4, 8, 11, 15, 18, and 22 after an intravenous injection of 10 mg/kg/dose of four-arm PEG-Gly-(7-ethyl-10-hydroxycamptothecin) or CPT-11 for five days. CPT-11 was also given 40 mg/kg/dose for five days. The results are set forth in FIG. 10. Multiple dose administration of four-arm PEG-Gly-(7-ethyl-10-hydroxycamptothecin) shows significant therapeutic efficacy compared to that of CPT-11. The results show that multiple doses of four-arm PEG-Gly-(7-ethyl-10-hydroxycamptothecin) is more effective than CPT-11 in the treatment of pancreatic cancer. Treatment with multiple doses of 4armPEG-Gly-(7-ethyl-10-hydroxycamptothecin) resulted in 95% TGI, whereas CPT-11 caused 34% TGI.

Example 31

In Vitro Metabolism

Figure 11:
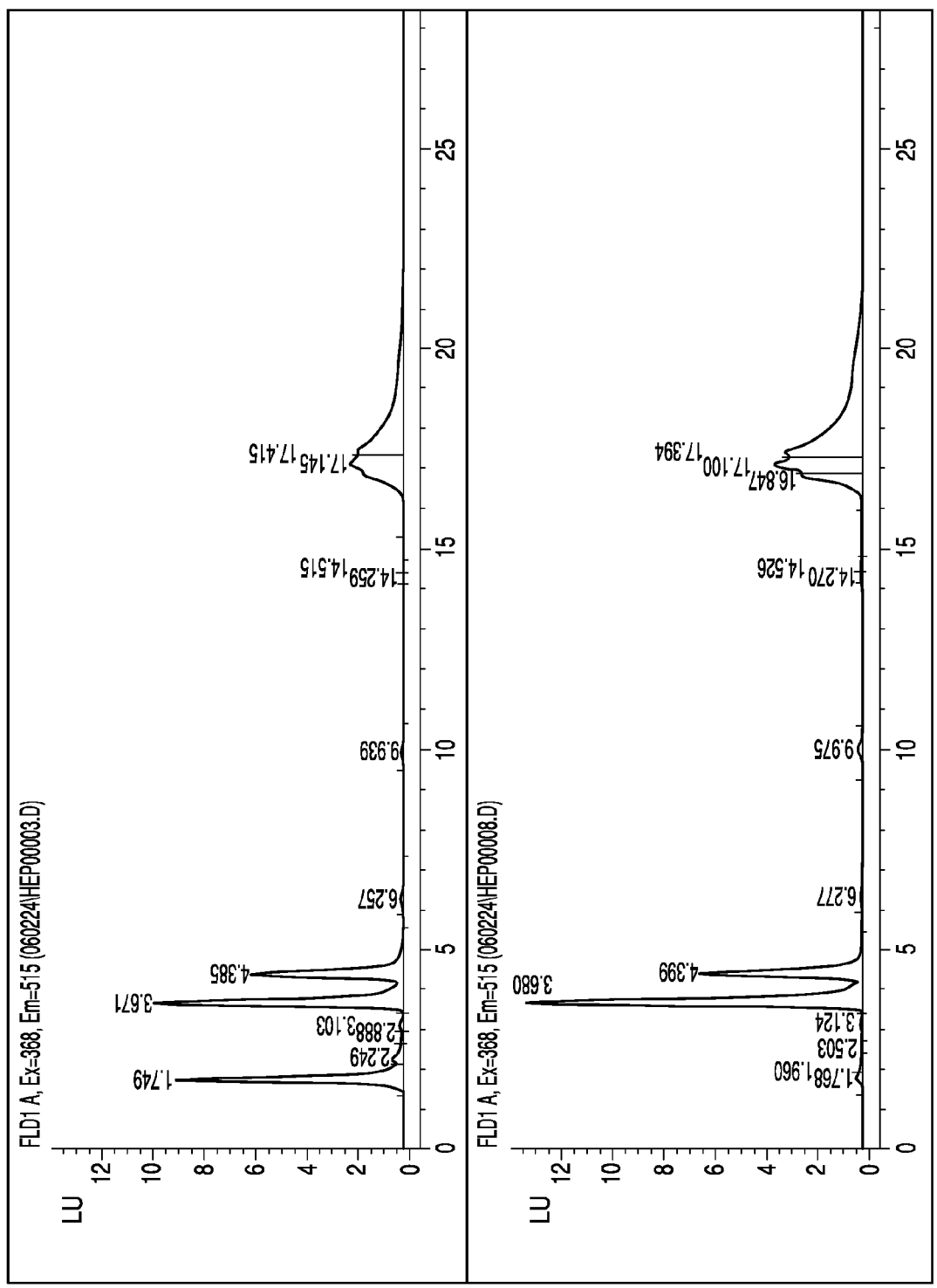
FIG. 11 shows in vitro metabolism of 4arm-PEG-Gly-(7-ethyl-O-hydroxycamptothecin) as described in Example 31.

In vitro metabolism of PEG-Gly-(7-ethyl-O-hydroxycamptothecin) conjugates was observed in rat hepatocytes. PEG-Gly-(7-ethyl-10-hydroxycamptothecin) was incubated with rat hepatocytes for 2 hours, pH 7.5, 37° C. As shown in FIG. 11, 7-ethyl-10-hydroxycamptothecin and 7-ethyl-10-hydroxycamptothecin-Glucuronide (7-ethyl-10-hydroxycamptothecin-G) were the major metabolites identified, which agrees with known metabolic pathway of 7-ethyl-10-hydroxycamptothecin in vivo.

Example 32

Properties of PEG Conjugates

Table 6 shows solubility of four different PEG-(7-ethyl-10-hydroxycamptothecin) conjugates in aqueous saline solution. All four PEG-(7-ethyl-10-hydroxycamptothecin) conjugates showed good solubility of up to 4 mg/mL equivalent of 7-ethyl-10-hydroxycamptothecin. In human plasma, 7-ethyl-10-hydroxycamptothecin was steadily released from the PEG conjugates with a doubling time of 22 to 52 minutes and the release appeared to be pH and concentration dependent as described in the following EXAMPLE 33.

TABLE 6

Properties of PEG-7-ethyl-10-hydroxycamptothecin Conjugates

| Compound | Solubility in Saline (mg/mL)$^a$ | $t_{1/2}$(min) in Human Plasma$^b$ | Doubling Time in Plasma (min)$^c$ | | |
|---|---|---|---|---|---|
| | | | Human | Mouse | Rat |
| Compound 9 (Gly) | 180 | 12.3 | 31.4 | 49.5 | 570 |
| Compound 12 (Ala) | 121 | 12.5 | 51.9 | 45.8 | 753 |
| Compound 23 (Sar) | ND | 19.0 | 28.8 | 43.4 | 481 |
| Compound 18 (Met) | 142 | 26.8 | 22.2 | 41.9 | 1920 |

$^a$7-ethyl-10-hydroxycamptothecin is not soluble in saline.
$^b$PEG conjugate half life.
$^c$7-ethyl-10-hydroxycamptothecin formation rate from conjugates.

PEG-7-ethyl-10-hydroxycamptothecin conjugates show good stability in saline and other aqueous medium for up to 24 hours at room temperature.

Example 33

Effects of Concentration and pH on Stability

Based on our previous work, acylation at the 20-OH position protects the lactone ring in the active closed form. The aqueous stability and hydrolysis properties in rat and human plasma were monitored using UV based HPLC methods. 4armPEG-Gly-(7-ethyl-10-hydroxycamptothecin) conjugates were incubated with each sample for 5 minutes at room temperature.

Figure 12:
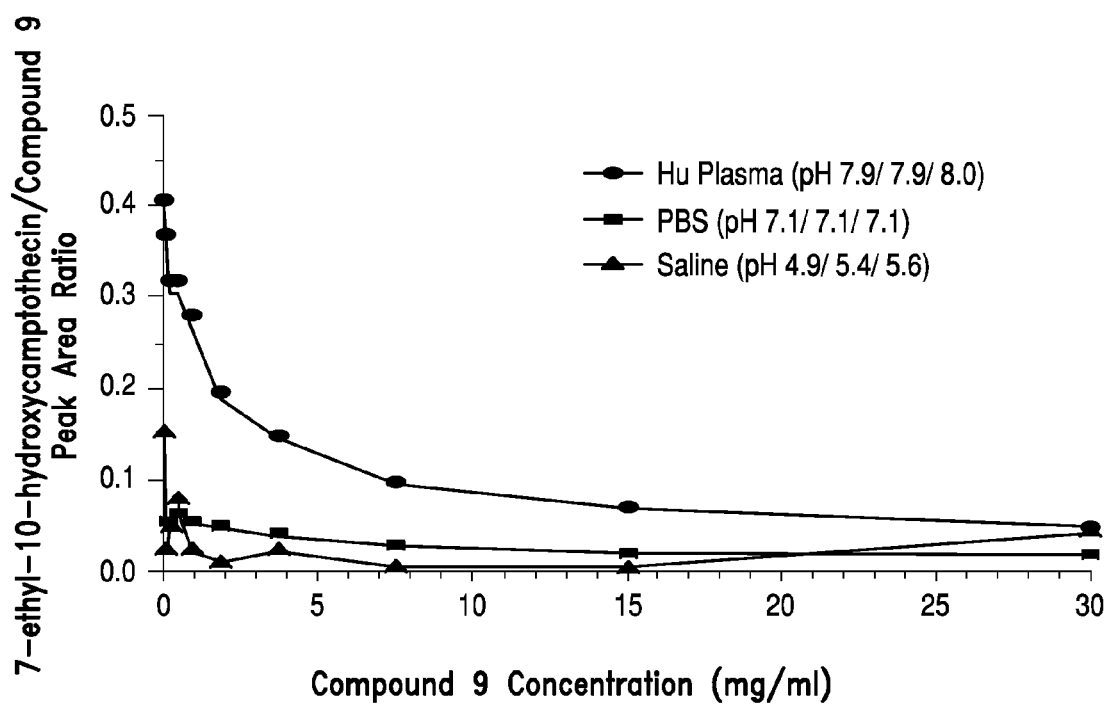
FIG. 12 shows stability of 4arm-PEG-Gly-(7-ethyl-10-hydroxycamptothecin) as described in Example 33.
Figure 13:
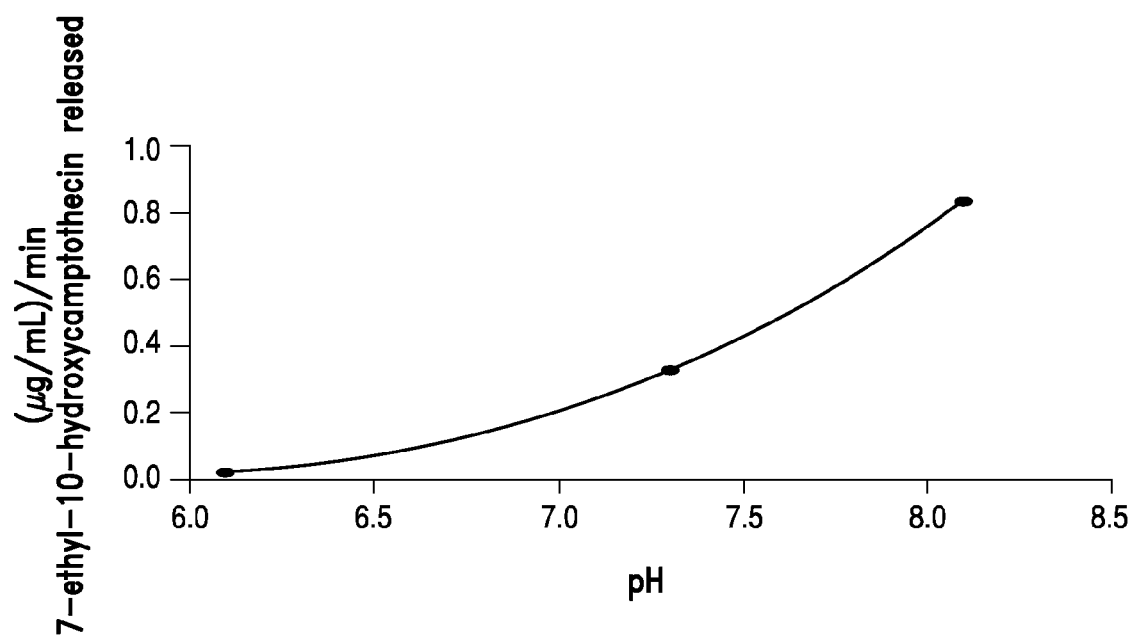
FIG. 13 shows effect of pH on stability of 4arm-PEG-Gly-(7-ethyl-10-hydroxycamptothecin) as described in Example 33.

Stability of PEG-7-ethyl-10-hydroxycamptothecin conjugates in buffer was pH dependent. FIG. 12 shows 4armPEG-Gly-(7-ethyl-10-hydroxycamptothecin) stability in various samples. FIG. 13 shows that rate of 7-ethyl-10-hydroxycamptothecin release from PEG-Gly-(7-ethyl-10-hydroxycamptothecin) increases with increased pH.

Example 34

Pharmacokinetics

Tumor free Balb/C mice were injected with a single injection of 20 mg/kg 4armPEG-Gly-(7-ethyl-10-hydroxycamptothecin) conjugates. At various time points mice were sacrificed and plasma was analyzed for intact conjugates and released 7-ethyl-10-hydroxycamptothecin by HPLC. Pharmacokinetic analysis was done using non-compartmental analysis (WinNonlin). Details are set forth in Table 7.

TABLE 7

Pharmacokinetic Data

| Parameter | Compound 9 | 7-ethyl-10-hydroxy-camptothecin Released from Compound 9 |
|---|---|---|
| AUC (h * μg/mL) | 124,000 | 98.3 |
| Terminal $t_{1/2}$ (Hr) | 19.3 | 14.2 |
| $C_{max}$ (μg/mL) | 20,500 | 13.2 |
| CL (mL/hr/kg) | 5.3 | 202 |
| Vss (mL/kg) | 131 | 3094 |

Figure 14:
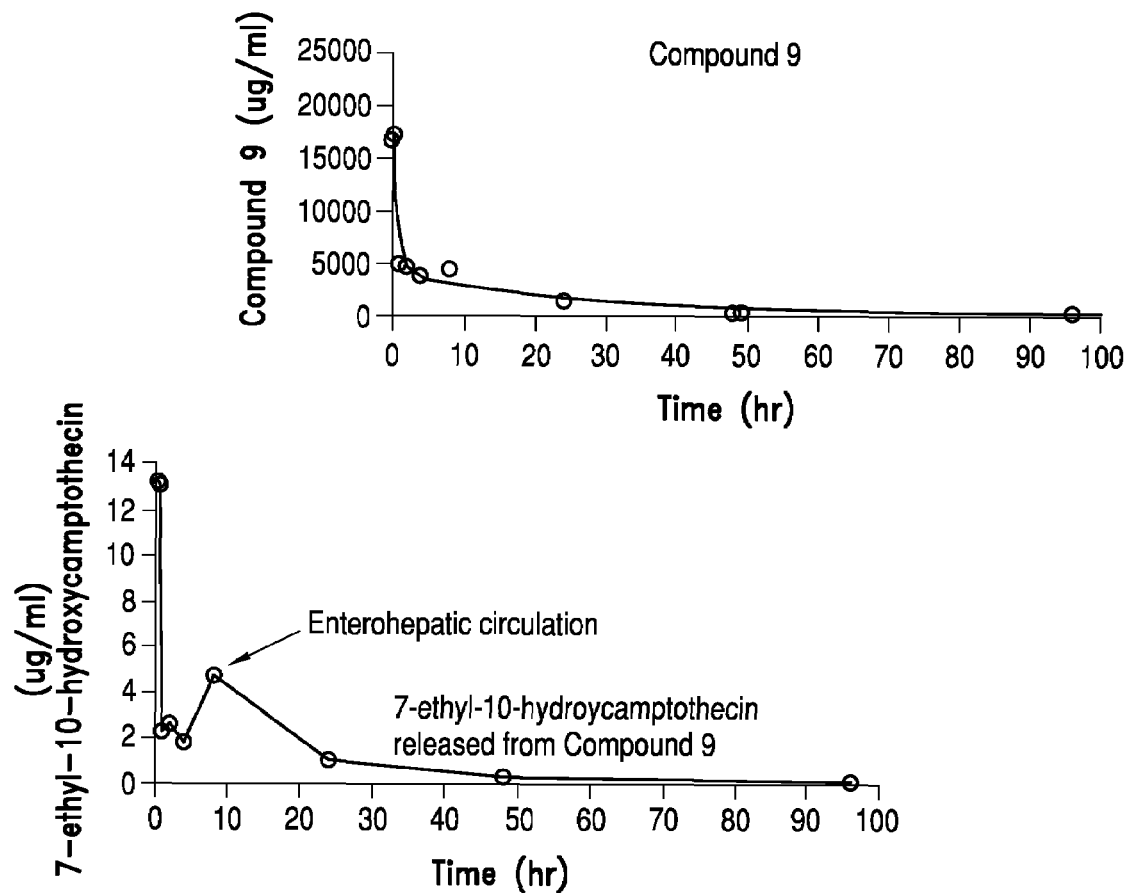
FIG. 14 shows pharmacokinetic profiles of 4arm-PEG-Gly-(7-ethyl-10-hydroxycamptothecin) as described in Example 34.

As shown in FIG. 14, pegylation of 7-ethyl-10-hydroxycamptothecin allows long circulation half life and high exposure to native drag 7-ethyl-10-hydroxycamptothecin. Enterohepatic circulation of 4armPEG-Gly-(7-ethyl-10-hydroxycamptothecin) conjugates was observed. The pharmacokinetic profile of PEG-Gly-(7-ethyl-10-hydroxycamptothecin) in mice was biphasic showing a rapid plasma distribution phase during the initial 2 hours followed by a 18-22 hours terminal elimination half-life for the conjugate and a concomitant 18-26 hours terminal elimination half-life for 7-ethyl-10-hydroxycamptothecin.

Additionally, pharmacokinetic profiles of 4arm PEG-Gly-(7-ethyl-10-hydroxycamptothecin) were investigated in rats. In rats, does levels of 3, 10 and 30 mg/kg (7-ethyl-10-hydroxycamptothecin equivalent) were used. The pharmacokinetic profiles in rats were consistent with those of mice.

In rats, 4arm PEG-Gly-(7-ethyl-10-hydroxycamptothecin) showed a biphasic clearance from the circulation with an elimination half life of 12-18 hours in rats. 7-ethyl-10-hydroxycamptothecin released from 4armPEG-Gly-7-ethyl-10-hydroxycamptothecin conjugates had an apparent elimination half life of 21-22 hours. The maximum plasma concentration ($C_{max}$) and area under the curve (AUC) increased in a dose dependent manner in rats. The apparent halflife of released 7-ethyl-10-hydroxycamptothecin from 4armPEG-Gly conjugates in mice or rats is significantly longer than the reported apparent half life of released 7-ethyl-10-hydroxycamptothecin from CPT-11 and the exposure of released 7-ethyl-10-hydroxycamptothecin from 4arm PEG-Gly-(7-ethyl-10-hydroxycamptothecin) is significantly higher than the reported exposure of released 7-ethyl-10-hydroxycamptothecin from CPT-11. The clearance of the parent compound was 0.35 mL/hr/kg in rats. The estimated volume of distribution at steady state (Vss) of the parent compound was 5.49 mL/kg. The clearance of the released 7-ethyl-10-hydroxycamptothecin was 131 mL/hr/kg in rats. The estimated Vss of released 7-ethyl-10-hydroxycamptothecin was 2384 mL/kg in rats. Enterohepatic circulation of released 7-ethyl-10-hydroxycamptothecin was observed both in mice and rats.

We claim:

1. A method of treating cancer in a mammal, comprising administering an effective amount of a compound of Formula (I)

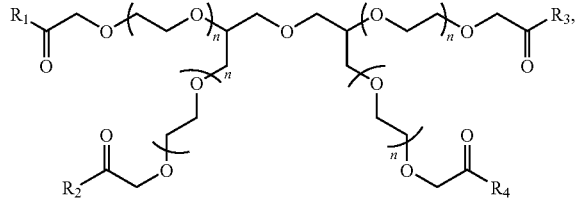

wherein
$R_1$, $R_2$, $R_3$ and $R_4$ are independently OH or $(L)_m$-D;
L is a bifunctional linker;
D is 7-ethyl-10-hydroxycamptothecin;
(m) is 0 or a positive integer from 1 to 10; and
(n) is a positive integer from about 28 to about 341,
provided that $R_1$, $R_2$, $R_3$ and $R_4$ are not all OH, to a mammal in need thereof.

2. The method of claim 1, wherein the cancer is metastatic.

3. The method of claim 1, wherein the cancer disease is selected from the group consisting of solid tumors, lymphomas, lung cancer, small cell lung cancer, acute lymphocytic leukemia (ALL), breast cancer, colorectal cancer, pancreatic cancer, glioblastoma, ovarian cancer and gastric cancer.

4. The method of claim 1, wherein (n) is from about 114 to about 227 so that the total molecular weight of the polymeric portion of the compound ranges from about 20,000 to about 40,000 daltons.

5. The method of claim 1, wherein (n) is about 227 so that the total molecular weight of the polymeric portion of the compound is about 40,000 daltons.

6. The method of claim 1, wherein the compound is administered in amounts of from about 1 mg/kg/week to about 100 mg/kg/week, and wherein the amount is the weight of 7-ethyl-10-hydroxycamptothecin included in the compound of Formula (I).

7. The method of claim 6, wherein the compound is administered in amounts of from about 2 mg/kg/week to about 60 mg/kg/week, and wherein the amount is the weight of 7-ethyl-10-hydroxycamptothecin included in the compound of Formula (I).

8. The method of claim 1, wherein the compound is administered in amounts of from about 5 to about 20 mg/kg/dose, and wherein the amount is the weight of 7-ethyl-10-hydroxycamptothecin included in the compound of Formula (I).

9. The method of claim 1, wherein the compound is administered in amounts of from about 10 to about 30 mg/kg/dose, and wherein the amount is the weight of 7-ethyl-10-hydroxycamptothecin included in the compound of Formula (I).

10. The method of claim 1, wherein D is

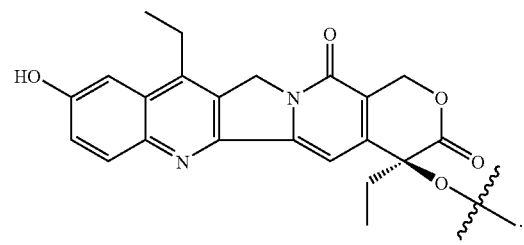

11. The method of claim 1, wherein L is an amino acid or amino acid derivative, wherein the amino acid derivative is selected from the group consisting of 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, N-ethylglycine, N-ethylasparagine, 3-hydroxyproline, 4-hydroxyproline, isodesmosine, allo-isoleucine, N-methylglycine, sarcosine, N-methyl-isoleucine, 6-N-methyl-lysine, N-methylvaline, norvaline, norleucine, and ornithine.

12. The method of claim 11, wherein L is glycine, alanine, methionine or sarcosine.

13. The method of claim 11, wherein L is glycine.

14. The method of claim 1, wherein L is selected from the group consisting of

—$[C(O)]_v NR_{21}(CR_{22}R_{23}O)_t$—,
—$[C(O)]_v NR_{21}(CR_{22}R_{23}O)_t(CR_{24}R_{25})_y O$—
—$[C(O)]_v NR_{21}(CR_{22}R_{23}O)_t(CR_{24}R_{25})_y$—,
—$[C(O)]_v NR_{21}(CR_{22}R_{23})_t O$—,
—$[C(O)]_v NR_{21}(CR_{22}R_{23})_t(CR_{24}CR_{25}O)_y NR_{26}$—,
—$[C(O)]_v O(CR_{22}R_{23})_t NR_{26}$—,
—$[C(O)]_v O(CR_{22}R_{23})_t O$—,
—$[C(O)]_v NR_{21}(CR_{22}R_{23})_t NR_{26}$—,
—$[C(O)]_v NR_{21}(CR_{22}R_{23})_t(CR_{24}CR_{25}O)_y$—,

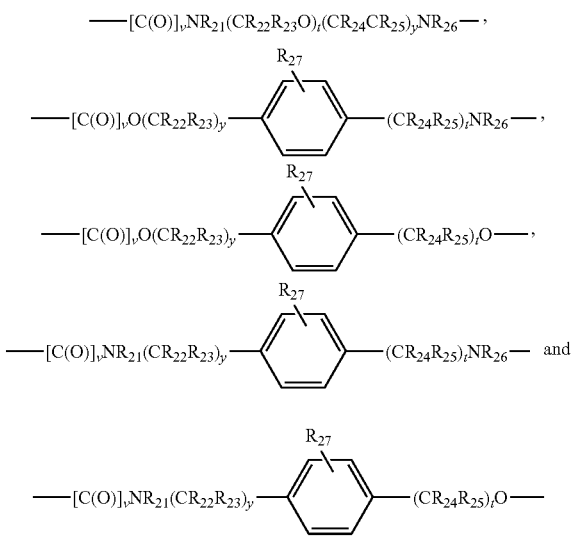

wherein:
R$_{21}$-R$_{26}$ are independently selected from the group consisting of hydrogen, C$_{1-6}$ alkyls, C$_{2-6}$ alkenyls, C$_{2-6}$ alkynyls, C$_{3-19}$ branched alkyls, C$_{3-8}$ cycloalkyls, C$_{1-6}$ substituted alkyls, C$_{2-6}$ substituted alkenyls, C$_{2-6}$ substituted alkynyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$heteroalkoxy;

R$_{27}$ is selected from the group consisting of hydrogen, C$_{1-6}$ alkyls, C$_{2-6}$ alkenyls, C$_{2-6}$ alkynyls, C$_{3-19}$ branched alkyls, C$_{3-8}$ cycloalkyls, C$_{1-6}$ substituted alkyls, C$_{2-6}$ substituted alkenyls, C$_{2-6}$ substituted alkynyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy, C$_{1-6}$ heteroalkoxy, NO$_2$, haloalkyl and halogen;

(t) and (y) are individually selected positive integers from about 1 to about 4; and (v) is 0 or 1.

15. The method of claim 1, wherein (m) is 1.

16. The method of claim 1, wherein R$_1$, R$_2$, R$_3$ and R$_4$ are (L)$_m$-D.

17. The method of claim 1, wherein the compound of Formula (I) is selected from the group consisting of

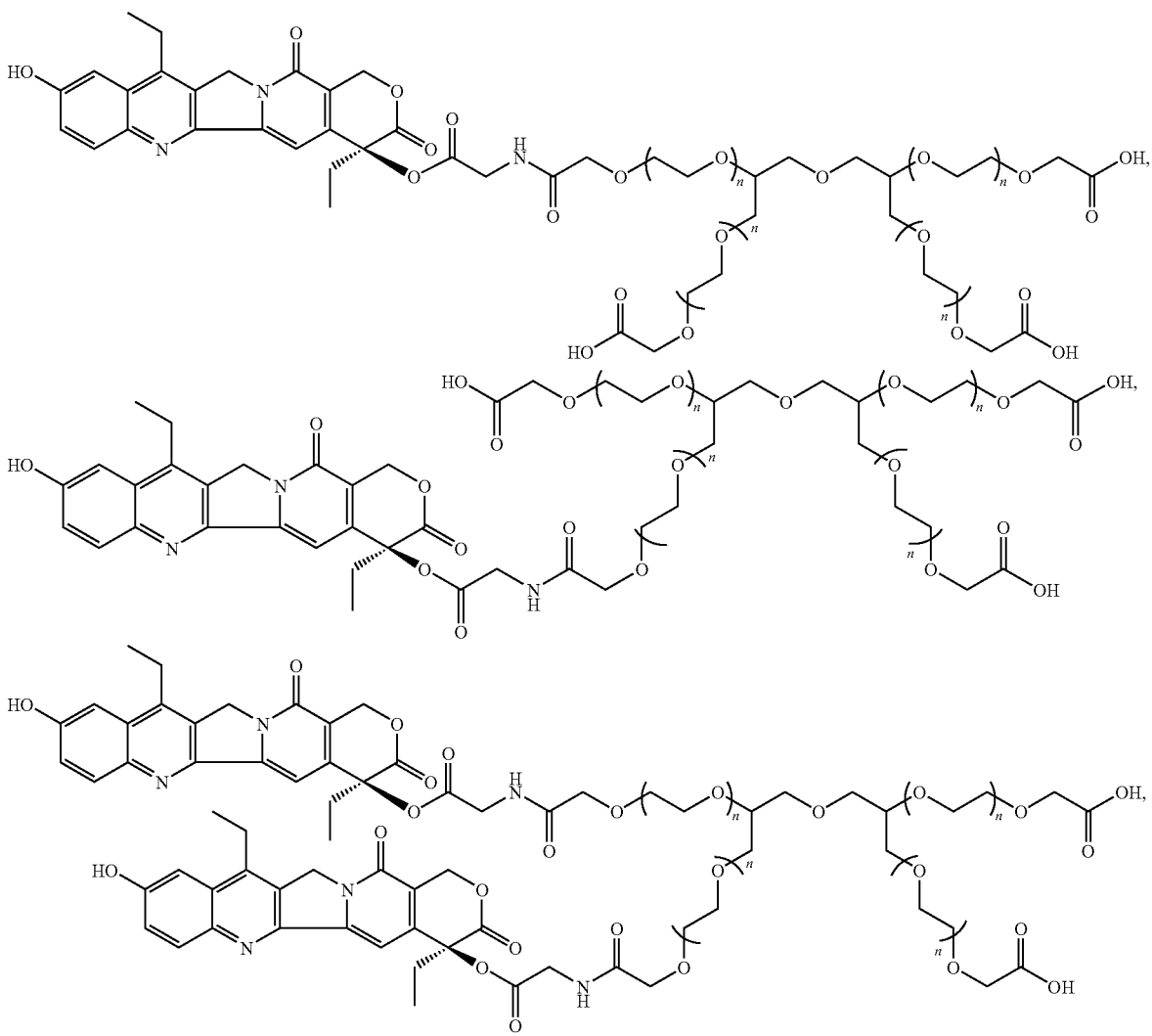

-continued
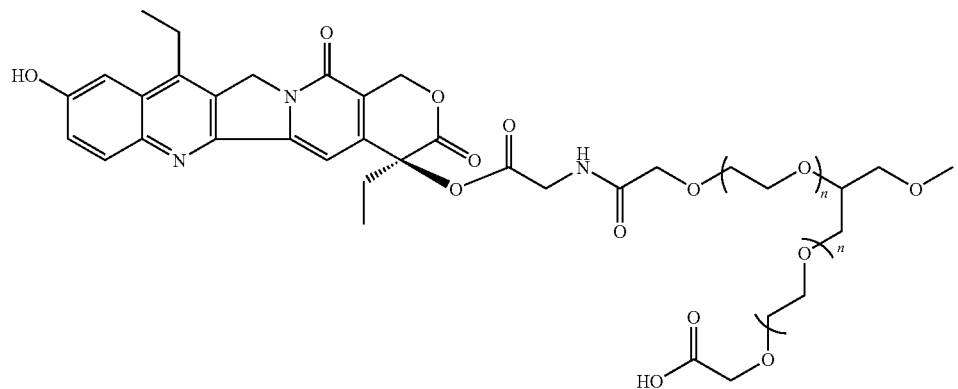
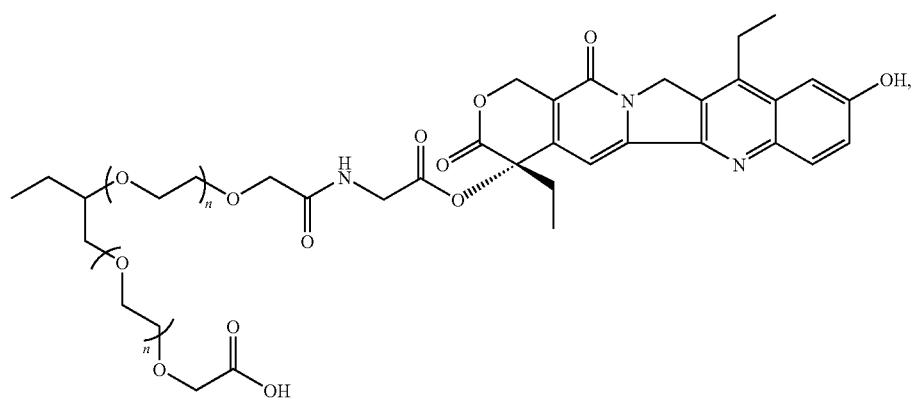
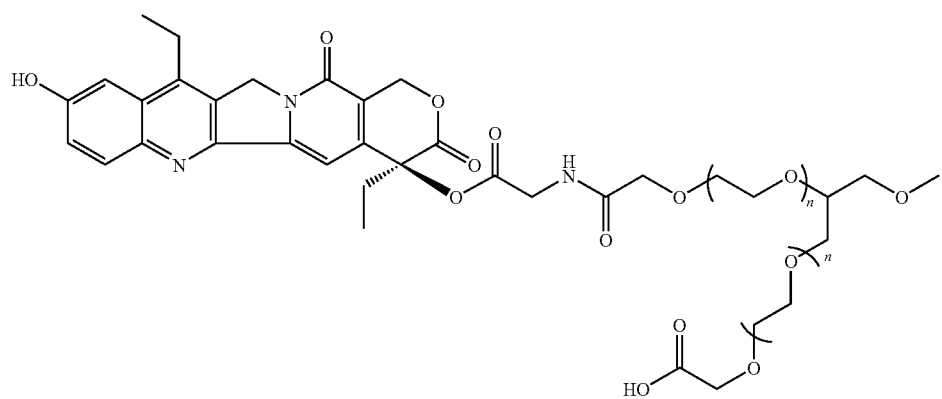
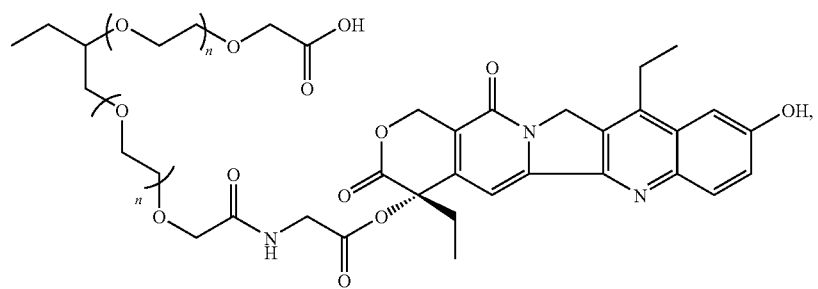

-continued
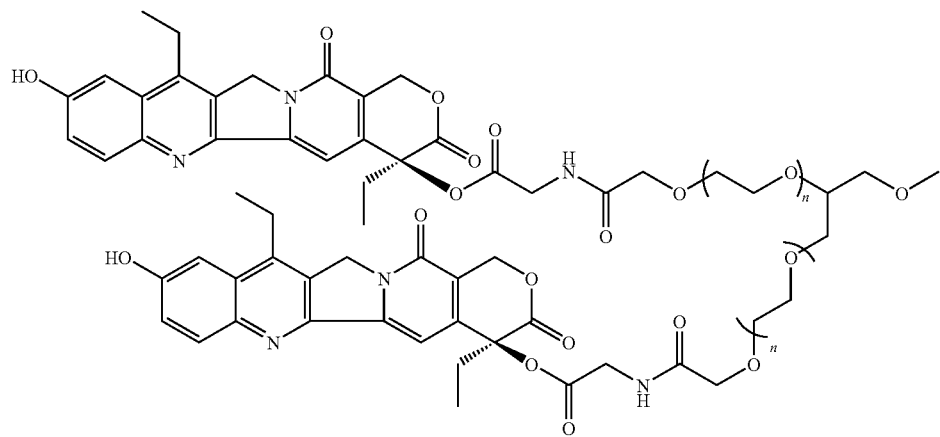
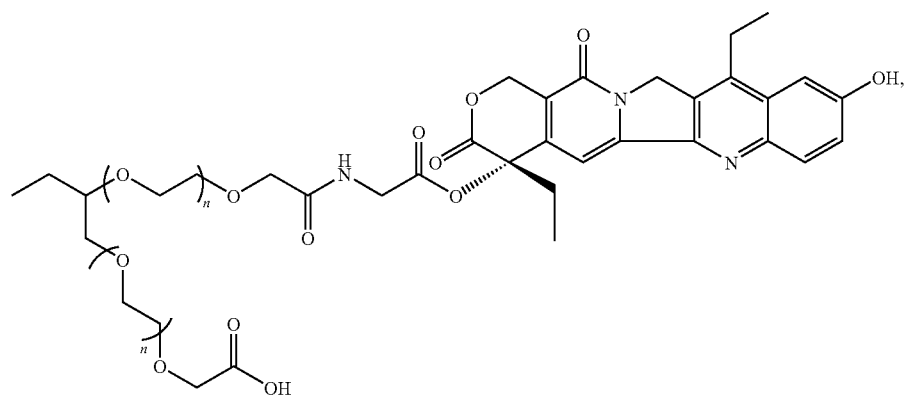
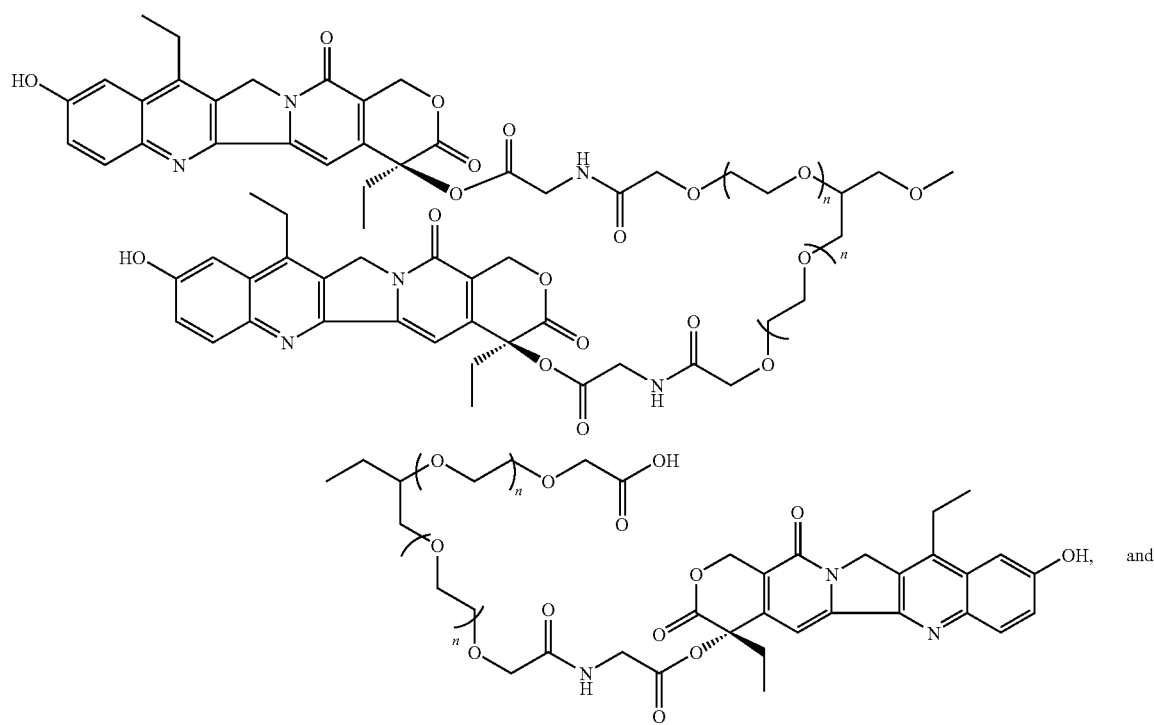

-continued
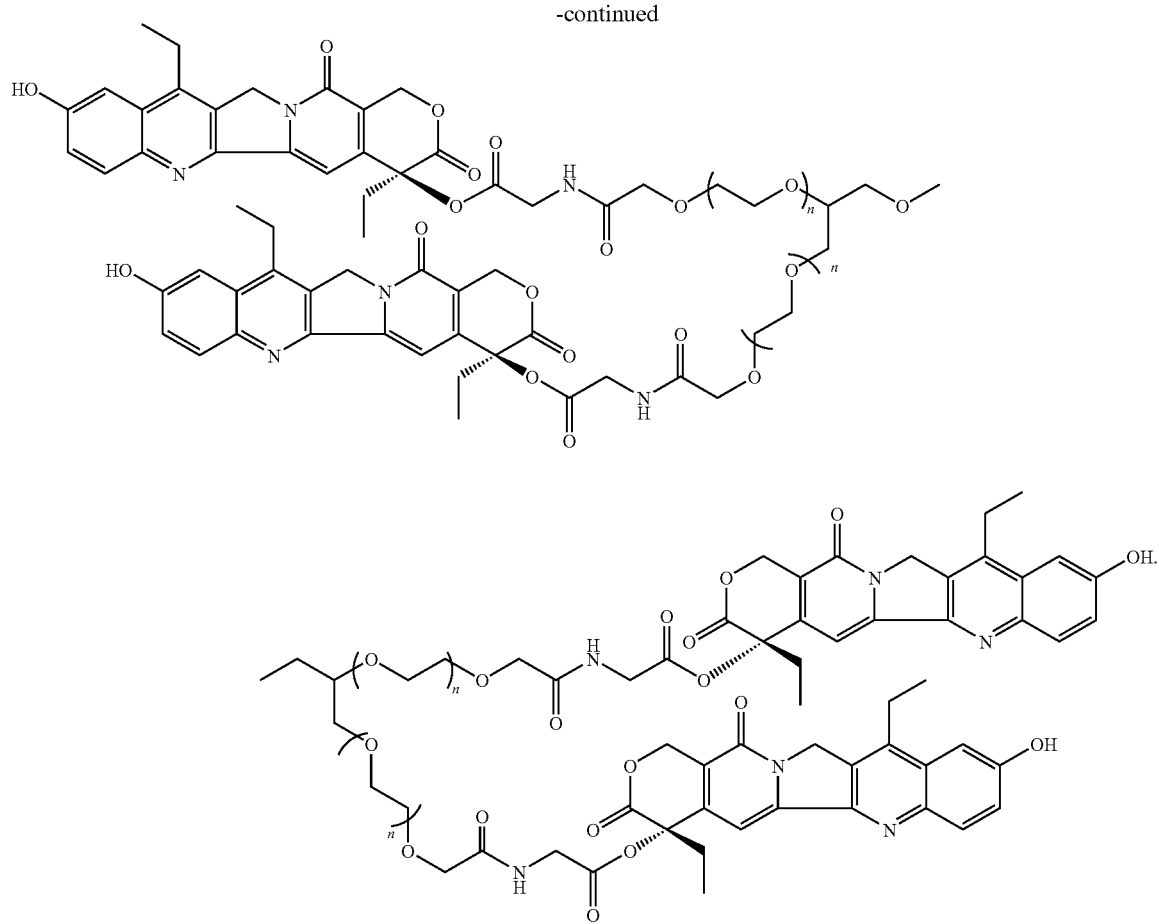
18. The method of claim 1, wherein the total molecular weight of the polymeric portion of the compound of formula (I) ranges from about 5,000 to about 60,000 daltons.
19. The method of claim 1, wherein the cancer is a solid tumor.
20. A method of treating cancer in a mammal, comprising administering an effective amount of a compound having the formula:
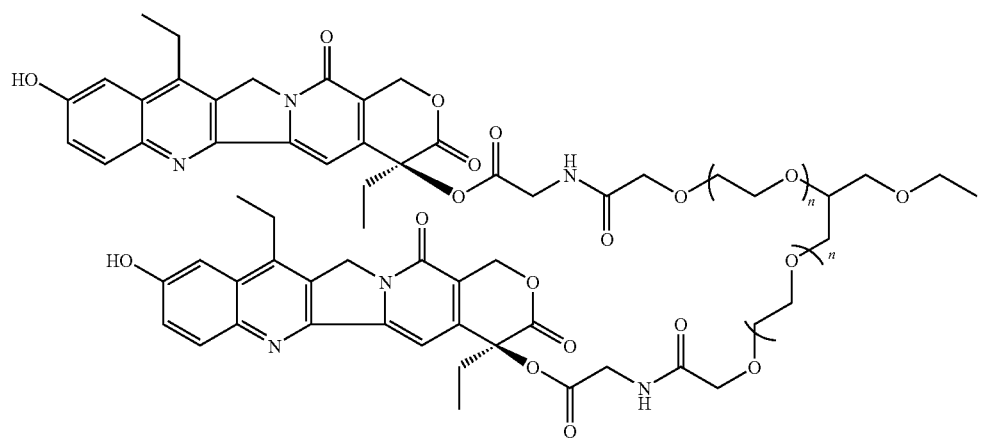

-continued

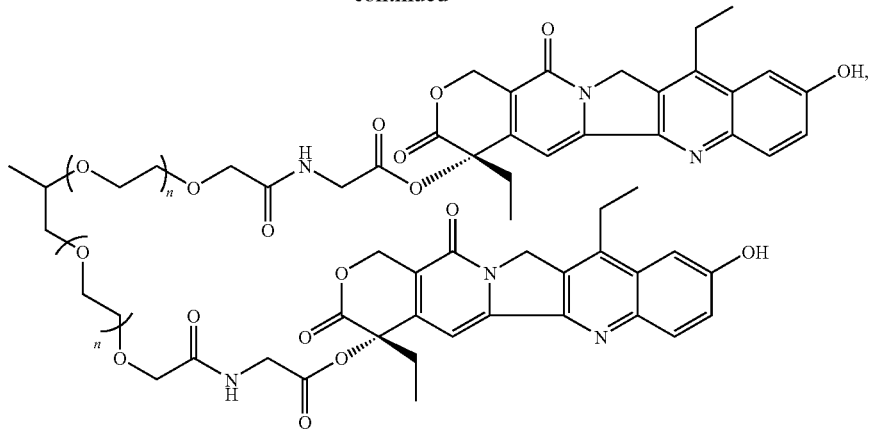

to a mammal in need thereof, wherein (n) is about 227 so that the total molecular weight of the polymeric portion of the compound is about 40,000 daltons.

21. The method of claim 20, wherein the cancer disease is selected from the group consisting of solid tumors, lymphomas, small cell lung cancer, acute lymphocytic leukemia (ALL), gastric cancer, lung cancer, breast cancer, colorectal cancer, pancreatic cancer, and ovarian cancer.

22. The method of claim 20, wherein the cancer is a solid tumor.

23. The method of claim 20, wherein the compound is administered in amounts of from about 1 mg/kg/week to about 100 mg/kg/week, and the amount is the weight of 7-ethyl-10-hydroxycamptothecin.

* * * * *